United States Patent
Brinkerhoff et al.

(10) Patent No.: US 9,962,307 B2
(45) Date of Patent: May 8, 2018

(54) ADJUSTABLE HAIR TRANSPLANTATION CHAIR

(75) Inventors: Mark D. Brinkerhoff, San Jose, CA (US); Robert A. Hines, Santa Cruz, CA (US); Gary R. Schultheis, Scotts Valley, CA (US); Eric R. Winger, Campbell, CA (US)

(73) Assignee: RESTORATION ROBOTICS, INC., San Jose, CA (US)

(*) Notice: Subject to any disclaimer, the term of this patent is extended or adjusted under 35 U.S.C. 154(b) by 1626 days.

(21) Appl. No.: 12/973,765

(22) Filed: Dec. 20, 2010

(65) Prior Publication Data

US 2012/0158138 A1 Jun. 21, 2012

(51) Int. Cl.
*A61G 15/02* (2006.01)
*A61G 15/00* (2006.01)
(Continued)

(52) U.S. Cl.
CPC .............. *A61G 15/00* (2013.01); *A61G 15/02* (2013.01); *A61G 15/125* (2013.01);
(Continued)

(58) Field of Classification Search
CPC .. B60N 2/02; A47C 1/00; A47C 13/00; A47C 7/50; A61G 15/12; A61G 15/125;
(Continued)

(56) References Cited

U.S. PATENT DOCUMENTS 2,153,763 A * 4/1939 Kuhler .................... B60N 2/10
248/395
3,989,297 A 11/1976 Kerstholt
(Continued)

FOREIGN PATENT DOCUMENTS

CN 2052227 U 2/1990
CN 2894442 Y 5/2007
(Continued)

OTHER PUBLICATIONS

PCT Int'l Search Report and Written Opinion Forms PCT/ISA/220, PCT/ISA/210 and PCT/ISA/237, in relation to commonly assigned PCT Application No. PCT/US2011/065166, dated Jun. 28, 2012. Applicant Restoration Robotics, Inc. (12 pages).
(Continued)

*Primary Examiner* — Ophelia A Hawthorne
*Assistant Examiner* — Camtu Nguyen

(57) ABSTRACT

A convertible chair, for example, a hair transplantation chair that permits movement of the patient during a procedure while the patient's head remains substantially stationary. The chair may include a head support and a plurality of body supports that may be mounted on a base, or on a cradle movably attached to the base. The chair can be configured for a follicular unit harvesting procedure and it could be also converted into a hair implantation configuration for hair implantation procedure. The patient remains in the chair during the procedure with his head substantially stationary, while various parts of his body may be repositioned, for example, by rotation of the cradle. The chair may be automated, or assisted with pneumatics, motors, foot pumps and the like. The chair is particularly useful for assisting robotic hair transplantation procedures.

25 Claims, 13 Drawing Sheets

(51) Int. Cl.
*A61G 15/12* (2006.01)
*A61B 17/00* (2006.01)

(52) U.S. Cl.
CPC ............. *A61B 2017/00752* (2013.01); *A61G 2200/325* (2013.01); *A61G 2200/327* (2013.01); *A61G 2200/56* (2013.01)

(58) Field of Classification Search
CPC .. A61G 15/02; A61G 13/121; A61G 13/1205; A61G 13/12; A61B 2017/00752
USPC ...... 128/845; 297/215.13, 411.35, 423.12, 1, 297/118, 283.1, 392, 423.11, 195.11, 325, 297/329, 215.15, 317, 322, 341, 342; 606/133; 5/621–622
See application file for complete search history.

(56) References Cited

U.S. PATENT DOCUMENTS

| | | | |
|---|---|---|---|
| 3,999,799 A * | 12/1976 | Daswick | 297/270.3 |
| 4,036,507 A * | 7/1977 | Henderson | B63C 13/00 |
| | | | 114/344 |
| 4,372,608 A | 2/1983 | Hotta | |
| 4,515,406 A * | 5/1985 | Fujiyama | A47C 7/38 |
| | | | 297/391 |
| 4,650,249 A * | 3/1987 | Serber | A47C 9/005 |
| | | | 248/397 |
| 4,736,982 A | 4/1988 | Hwang | |
| 4,746,167 A | 5/1988 | Palmer et al. | |
| 4,842,232 A * | 6/1989 | Pipon et al. | 248/395 |
| 4,918,767 A | 4/1990 | Benting | |
| 4,941,709 A | 7/1990 | Moller | |
| 4,971,040 A | 11/1990 | Gillotti | |
| 5,035,527 A | 7/1991 | Cheng | |
| 5,177,823 A | 1/1993 | Riach | |
| 5,186,519 A | 2/1993 | Larson | |
| 5,261,723 A | 11/1993 | Hosoe | |
| 5,261,725 A | 11/1993 | Rudolph | |
| 5,347,668 A | 9/1994 | Manning | |
| 5,348,375 A | 9/1994 | Steininger | |
| 5,401,078 A | 3/1995 | Riach | |
| 5,467,951 A | 11/1995 | Young | |
| 5,487,590 A | 1/1996 | Haynes | |
| 5,577,802 A | 11/1996 | Cowan et al. | |
| 5,667,278 A | 9/1997 | Li | |
| 5,673,970 A | 10/1997 | Homquist | |
| 5,762,402 A * | 6/1998 | Gillotti | A61G 15/007 |
| | | | 297/338 |
| D398,669 S | 9/1998 | Anderson et al. | |
| 5,884,350 A | 3/1999 | Kurze | |
| 5,921,696 A | 7/1999 | Gillotti | |
| 5,971,485 A | 10/1999 | Clark | |
| 6,022,076 A | 2/2000 | Samson | |
| 6,056,363 A * | 5/2000 | Maddox | 297/325 |
| 6,065,808 A | 5/2000 | Tinsley | |
| 6,382,725 B1 * | 5/2002 | Carroll | 297/330 |
| 6,422,649 B2 | 7/2002 | Hancock | |
| 6,450,578 B1 * | 9/2002 | Taggett | 297/325 |
| 6,543,853 B1 * | 4/2003 | Splane, Jr. | A47C 9/005 |
| | | | 297/195.11 |
| 6,595,589 B2 | 7/2003 | Cochran | |
| 6,619,747 B2 | 9/2003 | Ko et al. | |
| 6,641,214 B2 | 11/2003 | Veneruso | |
| 6,675,416 B2 | 1/2004 | Visser et al. | |
| 6,698,831 B2 | 3/2004 | Lloyd | |
| 6,729,690 B2 | 5/2004 | Roleder et al. | |
| 6,769,736 B2 | 8/2004 | Roleder et al. | |
| 6,802,564 B2 | 10/2004 | Brockway et al. | |
| 6,923,503 B2 | 8/2005 | Sangiorgio | |
| 7,017,996 B2 | 3/2006 | Peterson | |
| 7,036,882 B2 | 5/2006 | Elzenbeck | |
| 7,144,080 B2 | 12/2006 | Lloyd | |
| D555,249 S | 11/2007 | Roleder et al. | |
| D555,794 S | 11/2007 | Roleder et al. | |
| 7,311,353 B1 * | 12/2007 | Johnson | A47D 13/02 |
| | | | 280/30 |
| 7,311,359 B2 | 12/2007 | Smith | |
| 7,624,737 B2 | 12/2009 | Klemm | |
| D613,534 S | 4/2010 | Nordstrom | |
| 7,761,943 B2 | 7/2010 | Roleder et al. | |
| 8,474,848 B2 * | 7/2013 | Bernatsky et al. | 280/250.1 |
| 2002/0067060 A1 | 6/2002 | Lloyd | |
| 2003/0164459 A1 * | 9/2003 | Schardt | A61N 5/10 |
| | | | 250/492.3 |
| 2007/0052275 A1 * | 3/2007 | Ghilzai | A47C 1/06 |
| | | | 297/423.12 |
| 2010/0147314 A1 | 6/2010 | Lees | |

FOREIGN PATENT DOCUMENTS

| | | |
|---|---|---|
| CN | 101292824 | 10/2008 |
| CN | 101346081 | 1/2009 |
| EP | 1 555 005 | 7/2005 |
| WO | 1988/004149 | 6/1988 |
| WO | 2007/077191 | 7/2007 |

OTHER PUBLICATIONS

Extended European Search Report, in connection with commonly assigned European Patent Application No. 11851926.3, dated Dec. 10, 2013 [6 pages].
Office Action dated Jun. 24, 2014, in connection with commonly assigned Australian Patent Application No. 2011349716 (3 pages).
Office Action dated Jan. 23, 2015, in connection with commonly assigned Canadian Patent Application No. 2,818,531 (4 pages).
English Translation of Chinese Office Action dated May 11, 2015, in connection with commonly assigned Chinese Patent Application No. 201180057612.9, (2 pages).
English Translation of Office Action dated Nov. 10, 2015 in connection with commonly assigned Israeli Patent Application No. 226822, (2 pages).
Office Action dated Nov. 14, 2016, in connection with commonly assigned Canadian Patent Application No. 2,919,523 (3 pages).
English Translation of First Office Action, dated Oct. 31, 2016, in connection with commonly assigned Chinese Patent Application No. 201511020217.X (14 pages).

* cited by examiner

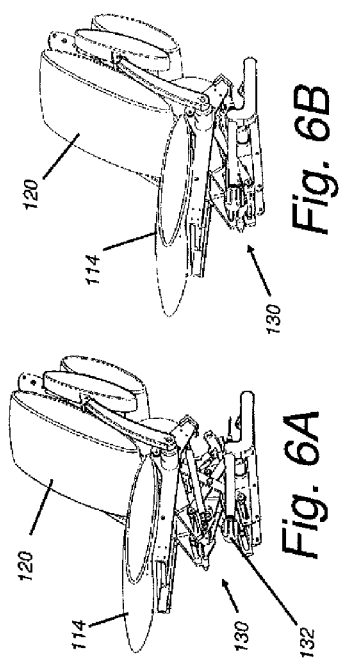
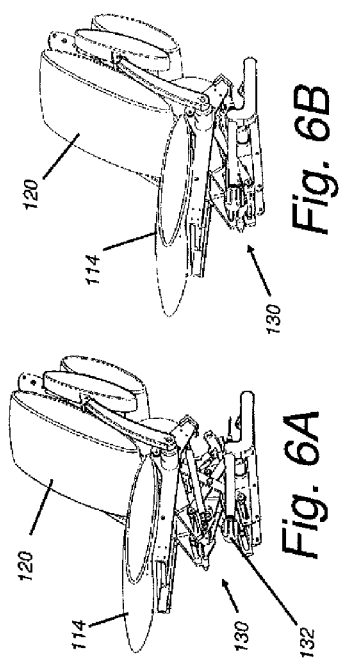
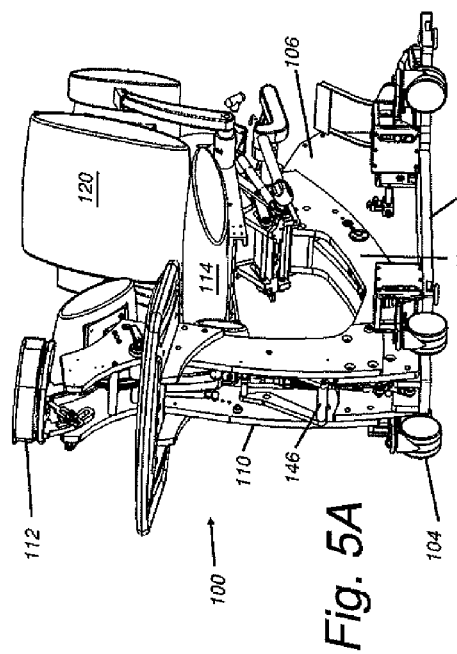
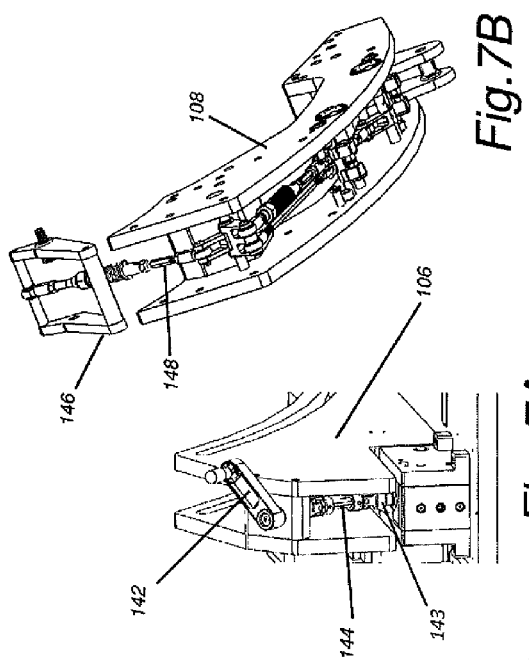
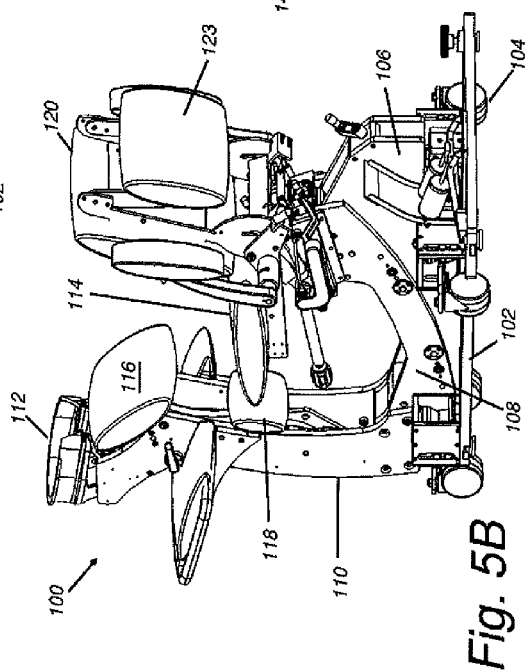

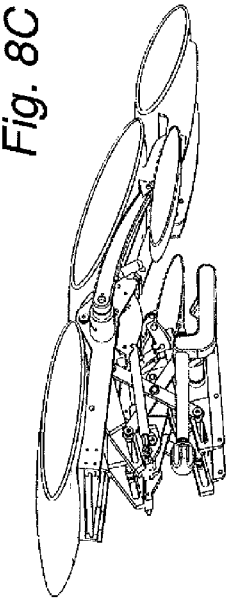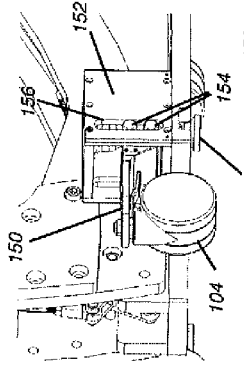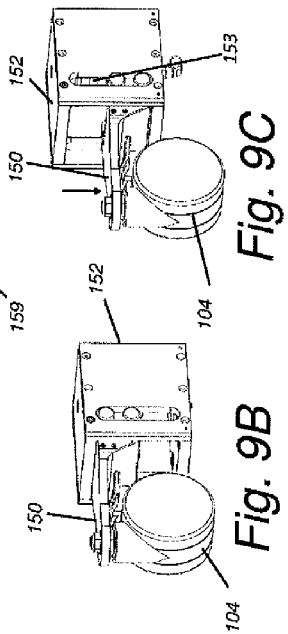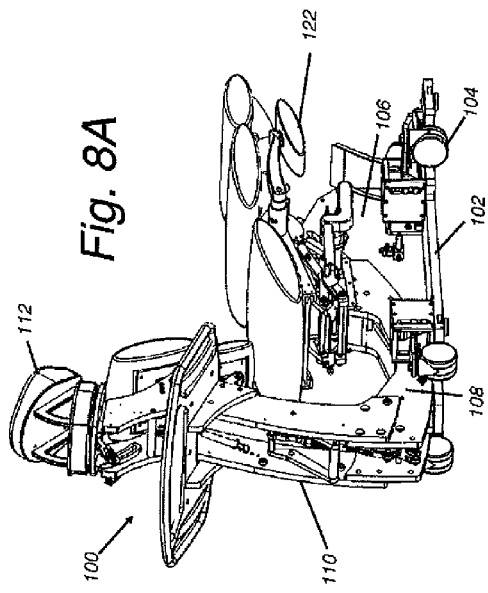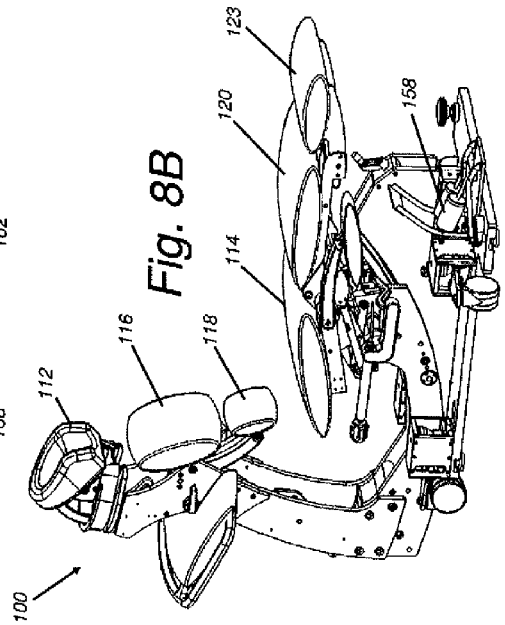

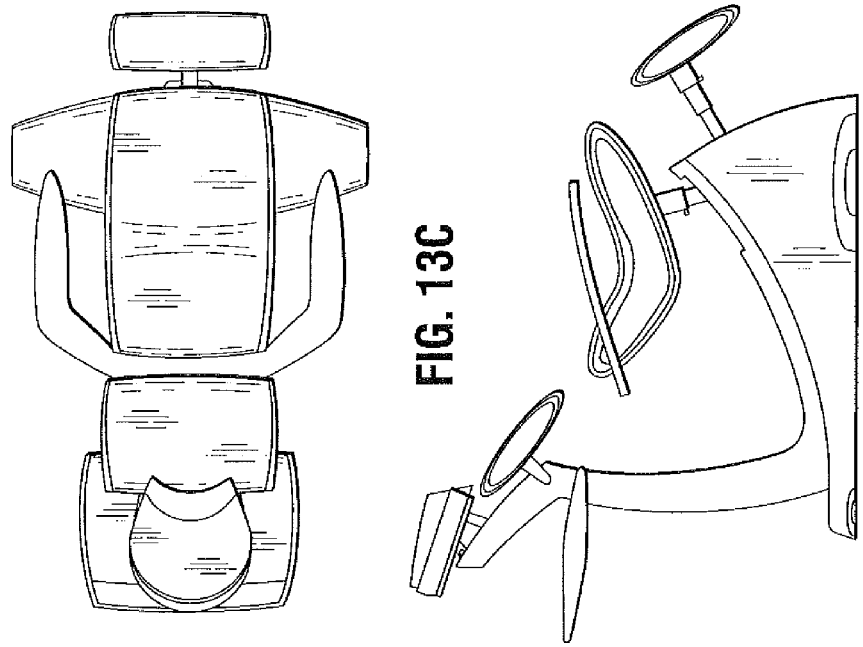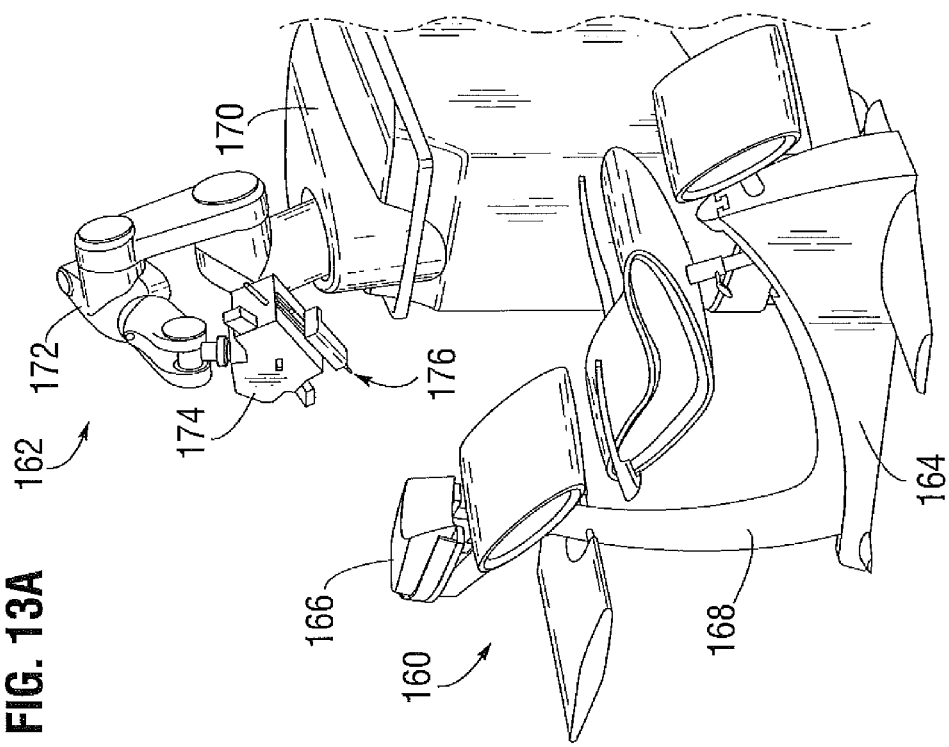

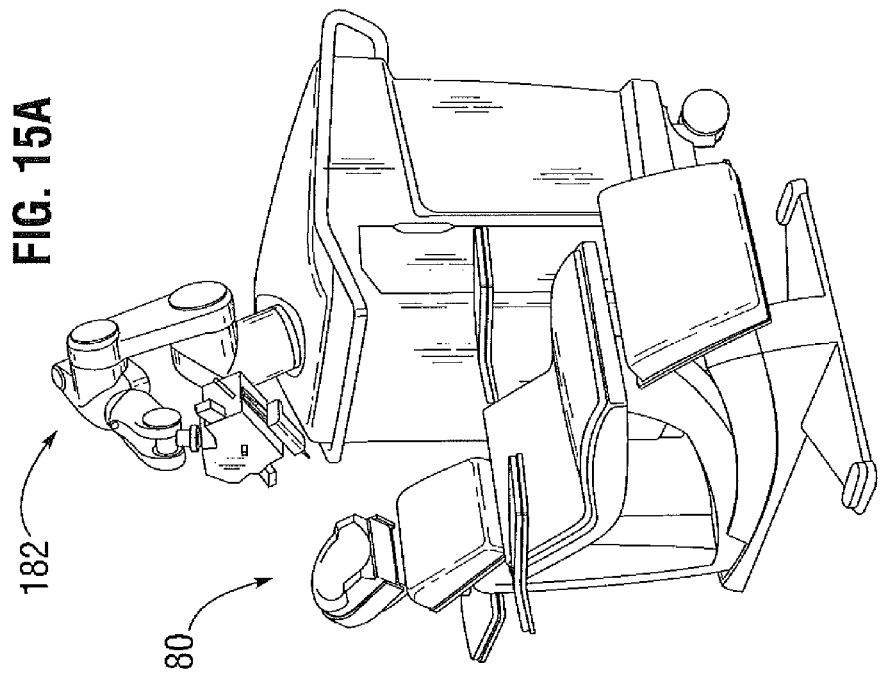
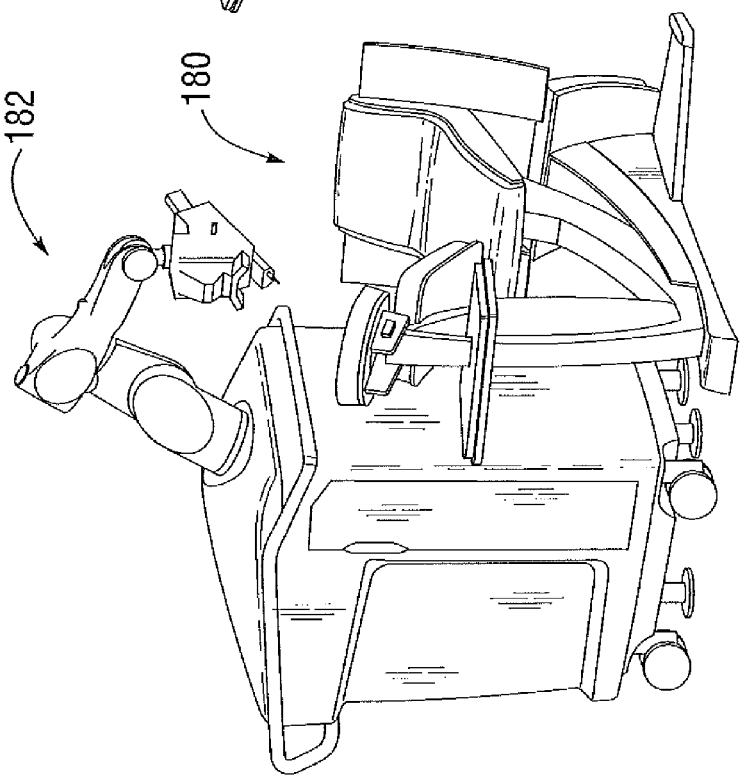

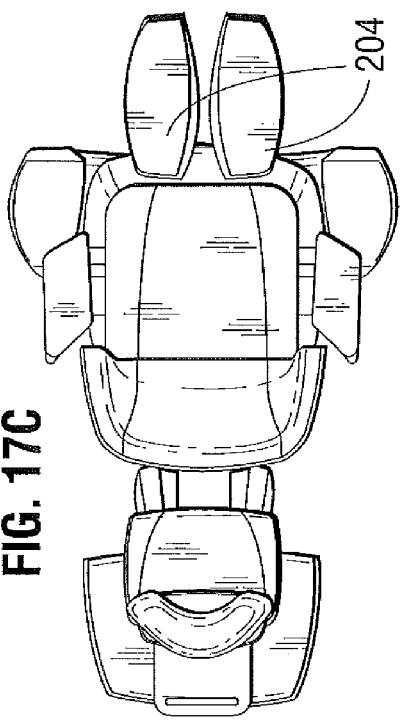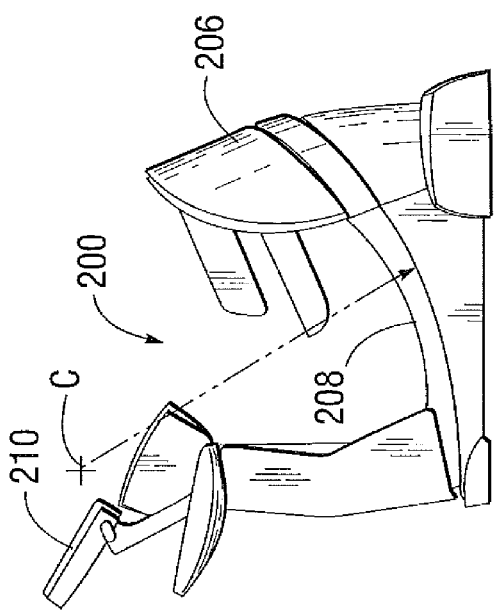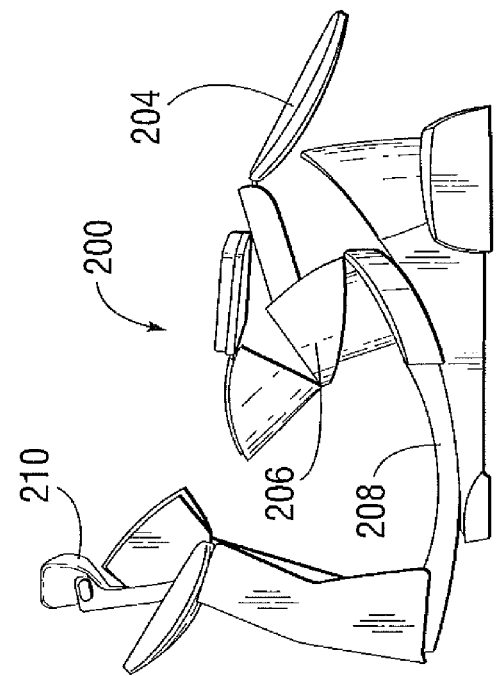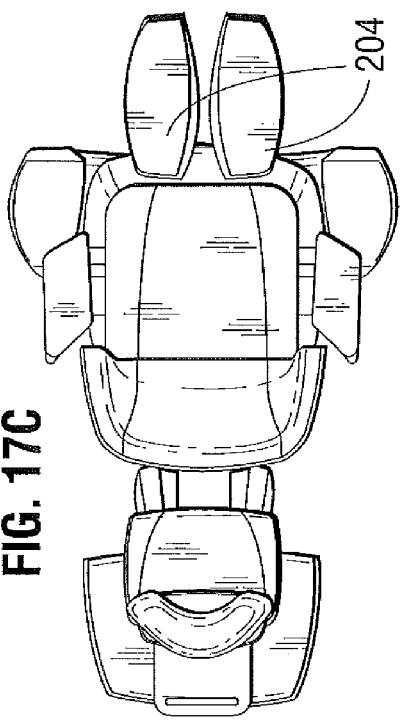

ADJUSTABLE HAIR TRANSPLANTATION CHAIR

FIELD OF THE INVENTION

This invention relates generally to adjustable chairs and, in particular, to a convertible and adjustable chair for use in hair transplantation procedures.

BACKGROUND OF THE INVENTION

A hair transplantation procedure typically involves harvesting donor hair grafts from a donor area, for example the side and back fringe areas of a patient's scalp, and implanting them in a bald area, or recipient area, for example, frontal hairline. There are various existing methods of performing hair harvesting, including, for example, a strip harvesting and the follicular unit extraction (FUE). In a strip harvesting procedure, the donor tissue (such as a strip of scalp) is removed under local anesthesia, the wound is sutured back together, and this piece of scalp tissue is then cut under a microscope into small pieces of tissue called grafts which are subsequently transplanted back into the thinning or bald area. FUE involves harvesting follicular units (FUs), which are naturally occurring aggregates of one to four closely-spaced hair follicles. Hair transplantation is a highly repetitive, time consuming and tedious procedure that could last many hours (e.g. whole day). In addition to hair transplantation procedures performed using manual or hand-held devices, the development of an image-guided robotic system for follicular unit extraction and implantation has been proposed, for example, in the commonly-assigned U.S. Patent Publication No. 2007/0106306 to Bodduluri et al.

The Bodduluri et al. '306 publication discloses a robotic system for harvesting and/or implanting FUs having a robotic arm and a tool (e.g. harvesting cannula or punch) operatively attached to the robotic arm. A robotic arm is positioned relative to a patient, so that a targeted body surface (in this instance, the donor area on the back of a patient's scalp) is within reach of a harvesting or implanting tool. The robotic system may include one or more cameras, and a processor receives and processes the images acquired thereby. A controller operatively associated with the processor precisely maneuvers the robotic arm to position the tool at desired locations and in desired orientations, for example, relative to follicular units targeted for harvesting from the scalp or at the desired implantation locations and orientations.

Hair transplantation surgery begins with injections of local anesthesia into the donor area. Once the donor area is numb, the doctor begins by removing a donor strip (in a strip harvesting procedure) or by harvesting individual follicular units (in an FUE procedures). Donor strip removal takes about 45 minutes and then it takes 3-4 hours for technicians to cut the donor strip into individual hair grafts for implantation, while individual FU removal may take 2-5 hours or longer depending on the amount of hair grafts needed and whether the harvesting is automated or not. During the harvesting part of the procedure, the patient must be positioned face-down for long periods of time.

During the implanting site making and hair graft implanting part of the procedure, the patient sits facing up for multiple hours, typically in a reclining surgical chair, or in a semi supine position on a surgery table. Current procedures typically utilize conventional adjustable dental chairs, such as the Boyd Oral Surgery Chair available from Boyd Industries of Clearwater, Fla.

Because of the length of the harvesting and implant procedures and due to the difficulties for the patient to remain in a stationary position during long periods of time, the patient may require many breaks to relax stiff muscles. Some of the drawback of such breaks is that they make the procedure even longer, and the patient rarely sits in exactly the same position when the procedure resumes. In particular for robotically-assisted procedures which may rely on precise imaging systems, these patient readjustments may require recalibration of the instruments. Therefore, what is needed is an improved patient positioning system for use in hair transplantation which both increases patient comfort during long periods of remaining stationary and reduces interruptions.

SUMMARY OF THE INVENTION

According to one general aspect, the chairs described herein allow to adjust position of a patient's body, for example, during hair harvesting, implantation, or transplantation procedures without substantially changing the position of the patient's head. The adjustments can be made with minimal interruptions of the procedure, or without any substantial increase in the time of the procedure.

According to one aspect, a chair is provided. The chair comprising a base and a cradle mounted on the base and configured for rotation along an arcuate path having a center located above the cradle. The chair further comprises a seat mounted on the cradle such that a person may be seated thereon with a head of the person on a head support, and the head support mounted at a location where a center of the head of the person, if positioned on the head support, is in a close proximity to the center of cradle rotation, wherein position of the cradle on the base being adjustable along the arcuate path such that the center of the head on the head support remains approximately at the center of cradle rotation.

In some embodiments the head support may be mounted to the cradle and in some embodiments it may be mounted to the base. The chair may be, for example, a hair transplantation chair. Furthermore, the hair transplantation chair may be implemented in the robotic hair transplantation procedures and also in the hair transplantation procedures where physician uses hand-held tools.

According to another embodiment a hair transplantation chair is provided that may comprise a base configured for placement on the ground and a head support mounted to the base near one end thereof. A cradle may be mounted on the base for rotation along an arc-shaped path having a center of rotation located above the cradle and in a vicinity of the head support, and a seat may be mounted on the cradle such that a person may be seated thereon with person's head on the head support. The position of the cradle on the base is adjustable along the arc such that a center of the head of the person when positioned on the head support remains approximately at the center of cradle rotation.

The present application also provides various methods for adjusting a chair and for performing procedures with the adjustable chair, for example, hair transplantation procedures. In some embodiments related to hair implantation, a method of performing a hair transplantation procedure may include positioning a person in a hair transplantation chair which has a head support for receiving the person's head in a face-up orientation. The chair further includes a cradle mounted on a base for rotation along an arc having a center located above the cradle, wherein the head support is mounted on the cradle such that a center of the person's head when positioned on the head support is approximately at the center of cradle rotation. A seat may be mounted, for example, closer to a second end of the cradle such that the person may be seated thereon with the head on the head support, and the position of the cradle on the base is adjustable along the arc such that the center of the head on the head support remains approximately at the center of cradle rotation. The method then involves adjusting the position of the cradle along the arc relative to the base and implanting follicular units, for example, to the patient's scalp while the patient is positioned in hair transplantation chair. In other embodiments of the methods of the present application, the above-described methodology may be implemented when harvesting follicular units. Furthermore, in either harvesting or implantation procedures, the steps of adjusting position of the cradle along the path may be repeated as needed to reposition the patient in the chair, and then the steps of hair harvesting or hair implantation may be repeated while the patient is in the adjusted position.

Another example of the method of performing a procedure (e.g., hair transplantation procedure) is a method comprising positioning a person in a chair, the chair having a head support for receiving the person's head in either a face-down orientation or a face-up orientation, the chair further including a cradle mounted on a base and configured for rotation along a substantially arc-shaped path having a center located above the cradle, wherein the head support is mounted such that when the person's head is positioned on the head support, a center of the head is approximately at the center of cradle rotation, and wherein a seat is mounted on the cradle such that the person may be seated thereon with his or her head on the head support, the position of the cradle on the base being adjustable along the arc such that the center of the head positioned on the head support remains approximately at the center of cradle rotation. The method further comprises adjusting position of the cradle along the substantially arc-shaped path relative to the base. The step of adjusting position of the cradle along the path may be repeated as needed to reposition the patient in the chair.

According to yet another aspect, a method for performing a hair transplantation procedure using a convertible hair transplantation chair is provided. The method comprises positioning a patient in a convertible hair transplantation chair in a harvesting configuration of the chair wherein a patient's posterior rests on a seat leaning forward with a head of the patient positioned face-down on a head support and harvesting follicular units from the patient positioned in the harvesting configuration of the convertible chair. The method further comprises converting the hair transplantation chair to an implantation configuration where the patient's posterior rests on the seat leaning backward with his head positioned face-up on the head support and implanting hair grafts into a recipient area of the patient in the implantation configuration of the convertible chair. In some embodiments, converting the chair comprises rotating at least a portion of the chair along an arcuate path with a center of rotation approximately near a center of a person's head when the head is positioned on the head support. Other and further objects and advantages of the invention will become apparent from the following detailed description when read in view of the accompanying figures.

BRIEF DESCRIPTION OF THE DRAWINGS

It should be noted that the drawings are not to scale and are intended only as an aid in conjunction with the explanations in the following detailed description. In the drawings, identical reference numbers, if any, identify similar elements or acts. The sizes and relative positions of elements in the drawings are not necessarily drawn to scale. For example, the shapes of various elements and angles are not drawn to scale, and some of these elements may be arbitrarily enlarged and positioned to improve drawing legibility. Features and advantages of the present invention will become appreciated as the same become better understood with reference to the specification, claims, and appended drawings wherein:

FIGS. 5A and 5B are perspective views from opposite sides of another example of an adjustable hair transplantation chair of the present application in a harvesting position;

FIGS. 6A and 6B illustrate an example of the seat of the chair of the present application and an example of its elevation mechanism in raised and lowered positions, respectively;

FIG. 7A is a detail view of an example of an embodiment of a crank adjustment mechanism that may be implemented to rotate a cradle of the hair transplantation chair, such as that shown in FIGS. 5A and 5B, and FIG. 7B is a detail view of an example of a locking mechanism for the cradle;

FIGS. 8A and 8B are perspective views from opposite sides of the hair transplantation chair of FIGS. 5A and 5B re-configured into an implantation position, and FIG. 8c illustrates just an example of the seat of the chair and its elevation mechanism thereof;

FIGS. 9A-9C are several views of an example of an adjustment structure for attaching and/or adjusting wheels of the hair transplantation chair that may be implemented in various embodiments;

FIGS. 13A-13C are perspective and orthogonal views of the hair transplantation chair of FIGS. 12A-12C in an implant position, also illustrating the robotic system used for automated hair transplantation;

FIGS. 14A-14C are perspective and orthogonal views of a still further adjustable hair transplantation chair of the present application in a harvesting position, also illustrating a robotic system used for automated hair harvesting;

FIGS. 15A-15C are perspective and orthogonal views of the hair transplantation chair of FIGS. 14A-14C, also illustrating a robotic system used for automated hair implantation;

FIGS. 16A-16C are perspective and orthogonal views of a still further adjustable hair transplantation chair of the present application in a harvesting position, also illustrating a robotic system used for automated hair harvesting;

FIGS. 17A-17C are perspective and orthogonal views of the hair transplantation chair of FIGS. 16A-16C, also illustrating a robotic system used for automated hair implantation.

DETAILED DESCRIPTION OF THE PREFERRED EMBODIMENTS

Figure 1:
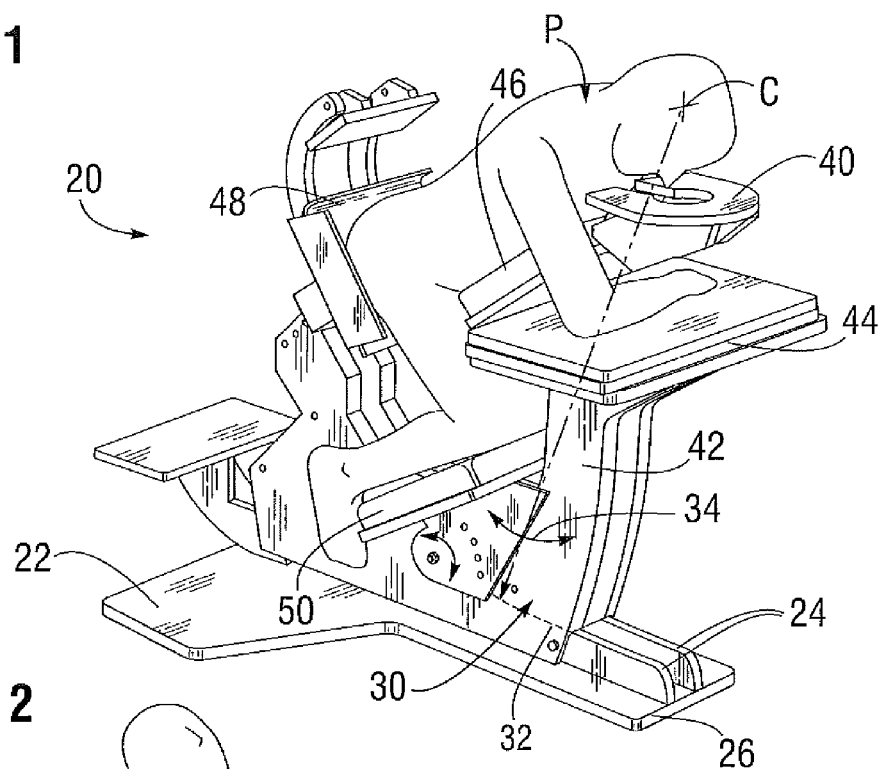
FIG. 1 is a perspective view of a patient positioned in an adjustable hair transplantation chair according to one embodiment of the present application configured for a hair harvesting procedure.

In the following Detailed Description, reference is made to the accompanying drawings that show by way of illustration some examples of embodiments in which the invention may be practiced. In this regard, directional terminology, such as "right", "left", "upwards", "downwards", "forward", "backward", "vertical", "horizontal" etc., are used with reference to the orientation of the Figure(s) being described. Because components or embodiments of the present invention can be positioned or operated in a number of different orientations, the directional terminology is used for purposes of illustration and is in no way limiting. The terms "operatively connected," "coupled," or "mounted," or "attached" as used herein, means directly or indirectly coupled, attached, or mounted through one or more intervening components. It is also to be understood that other embodiments may be utilized and structural or logical changes may be made without departing from the scope of the present invention. The following description, therefore, is not to be taken in a limiting sense, and the scope of the present invention is defined by the appended claims.

Many medical procedures, for example, hair restoration, is a time-consuming process that can take in some cases all day. Hair transplantation typically involves hair harvesting and hair implantation (which may include making small holes in a bald area where follicular units will be implanted, sometimes called "site making"). Robotic implementation of any or all parts of the procedure may greatly speed up the overall process. The present application is directed to a chair and methods of its use that are especially useful in hair transplantation procedures. According to one aspect, a hair transplantation chair is provided that can be used and adjusted for both the harvesting and implantation procedures.

The hair transplantation chairs described herein are especially beneficial in the automated, e.g. robotic, procedures, however, they are useful for both manual and robotic hair transplantations, as the issue of the patient's comfort applies to both. For instance, these procedures often require access to the sides of the patient's scalp/donor area while holding the head stable with minimal movement. For example, the patient may need to rotate/turn their head 45° in order for the automated harvesting device to harvest the sides of the scalp. Applicant is not aware of any chairs on the market which are specifically designed for use in hair transplantation procedures or any current chair configuration for use in other applications that fulfills the needs of patient positioning during hair transplantation procedures.

The various chairs described herein desirably address a number of deficiencies of the chairs currently available on the market for use in different applications. First of all, it should be understood that a patient chair for hair transplantation has some unique requirements that are not relevant or present in various chairs that exist on the market (including various massage chairs, surgical chairs, etc.) The hair transplantation procedure is very time consuming (current manual procedures may last the whole day—8 hours!) and the patient is usually awake during the procedure (unlike patients under anesthesia in some surgical procedures). The patient thus tends to move around during that lengthy procedure. Patient movement during a massage session, for example, is of no serious consequence, and indeed may be encouraged. Therefore massage chairs are designed without addressing concerns of patient movement. However, in hair transplantation, and especially in the robotic hair transplantation, it is important to reduce movements of the head of a patient during operation of the harvesting or implanting tools to avoid injuries and assure precise placement of the tool to harvest or implant hair grafts. At the same time, while the chairs described herein are especially useful for hair transplantation, they could be also used in other procedures where the same considerations apply—the patient is generally awake (not under general anesthesia like in most surgeries), the procedure is lengthy and it is hard for the patient to remain still for a long time, and where it is important that the patient's head is positioned at a certain level at all times with minimal movement. For example, certain cosmetic surgery procedures may benefit from the adjustable chairs described herein.

The chairs described in the present application provide a chair architecture that enables the patient to sit for a significant period of time with his head in substantially the same position, and at the same time allow the patient to reduce patient fatigue, pain, discomfort, or soreness from sitting in any one position for an extended period of time. This goal is achieved with a configuration that allows the chair to essentially "pivot" approximately about the head of the patient, thus allowing the patient to pivot his/her position as a whole and eliminate fatigue without actually moving the head relative to the body positioning. The "pivoting" allows change of the patient's center of gravity so as to relocate sitting pressures to different parts of the body, which accomplishes the same goal as if the patient moved.

The present application provides a chair architecture that enables the head of the patient to essentially remain in substantially the same position despite any motion of the chair, so that a manual hand-held tool, or a robotic arm with the attached tool can continue to access the head, for example, without having to undergo major recalibration, and so that time is not wasted on repositioning the tool.

According to another aspect, a chair architecture is provided that enables the doctor to access the patient's head, and the patient's head remain in substantially the same position, despite any motion of the chair. At the same time, it allows the doctor to remain comfortable during the long procedure. For example, while the patient's body position is adjusted, a doctor may be standing or seated during the procedure in the same position without a need to change the elevation of his/her hands to accommodate movement of the patient's head. An architecture that substantially allows the chair to "pivot" about the head of the patient such that the head remains at approximately the same level or position achieves this objective.

According to a further aspect, a chair architecture is provided that can be utilized for both the hair harvesting procedure in which the patient has his face down, and the hair implanting procedure in which the patient has his face up. The chairs described herein reduce the chair space required in the treatment office by providing a chair design that is capable of comfortably supporting a patient in both harvesting and implanting positions. The disclosed chairs provide for adjusting position of the patient's body during both harvesting and implantation without slowing down either procedure.

In certain embodiments, a central structure of the chair (a cradle mechanism) typically supports functional areas of the chair, such as a seat and a head support. The central structure also provides an adjustment, which addresses the need to position the patient in both face-up (implantation) and face-down (harvesting) positions. This positioning also enables different body sizes to be accommodated comfortably. It is also anticipated that patient body fatigue will be somewhat relieved by re-positioning of the patient during the procedure as described in detail below.

One of the purposes of the chair is to position the patient's head for both robotic and physician access. The chair will position the patient's head within the range and capability of the robotic arm with the attached tool for dissection and/or site making/implanting. The chair will also position the patient's head for accessibility by the physician and technicians for manual harvesting and manual implanting.

The size of the chair, its configuration and build-in adjustments are designed to accommodate a male in the 5% to 95% physical demographic. (The 5% to 95% range, is taken from statistical data giving various heights relative to a male person seated on a chair in various positions). According to some embodiments, the chair is designed to essentially provide a pivoting or rotating motion approximately about the head of this "5% to 95% male", for example, when the head is positioned on a head support of the chair. In some embodiments, the chair is configured such that a pivoting (or center of rotation) point may be at an elevation approximately in a range of around 44 to 48 inches or so from the floor or the ground level. One of the functions of the chair rotation according to the present application is to maintain the height of the top of the head, or the area in which the procedure is accessible, within the range that does not interfere with the robotic arm. In the embodiments mentioned earlier in this paragraph, it may be desirable to keep the top of the head at a height, for example, between 48 to 52 inches from the floor. This provides desired accessibility for the doctor and keeps it within the operational range of the robotic arm. In this example, the center of rotation may be approximately at 46 inches from the floor, and the radius of the arch may be approximately at 44 inches. Variations, of course, will occur due to various factors, including without limitation head size, site location, particular medical procedure involved, head support adjustment features, in particular sliding front to back and pivoting within the head support itself. In this position of the center of rotation or pivoting, some physicians will stand during procedure while some physicians can sit, for example on a high chair, and have convenient access to the patient's head (instead of standing on his/her feet for hours). At the same time, in the robotic implementation, position of the pivoting point at certain height above the floor (for example, 44 to 48 inches from the ground) permits the robotic arm to move freely above and around the patient's head without interfering with the head or causing any undesirable contact (proper "clearance" distance). Furthermore, the chairs of the present application allow for easy patient's entry and exit from the chair.

In addition to providing rotational repositioning of the whole body of a patient so that it is comfortable for treatment, the chair of the present application may provide, for example, for various independent adjustments to the chest, seat, arms, and ankles. Some of these adjustments may be indexed while some may be infinite depending on the embodiment of the chair and associated methods of chair movement and adjustments.

Figure 2:
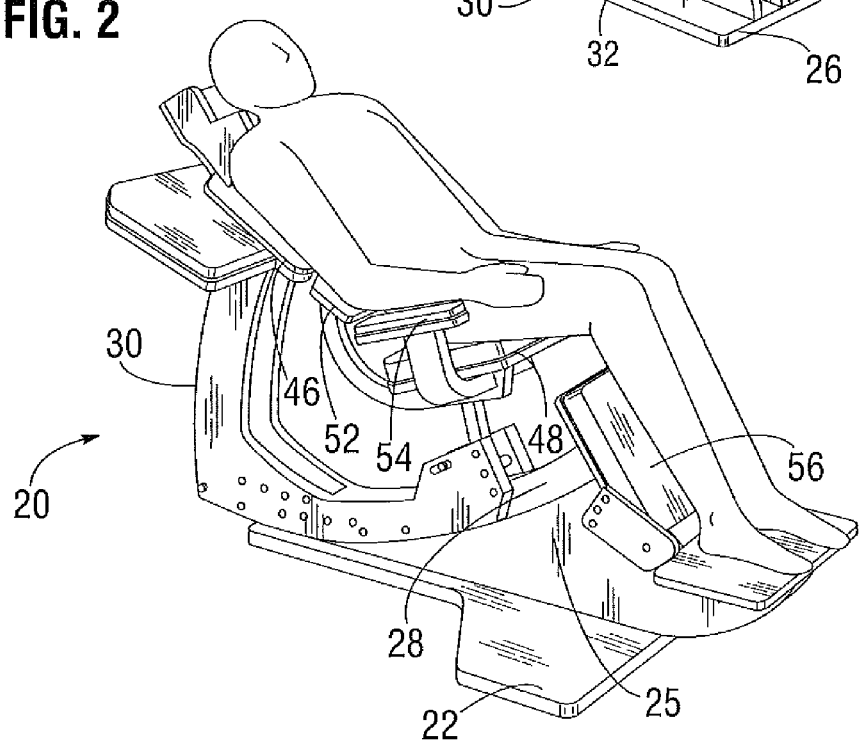
FIG. 2 is a perspective view of a patient positioned in the hair transplantation chair of FIG. 1 re-configured for an implantation procedure.

FIGS. 1 and 2 illustrate a patient P in an adjustable hair transplantation chair 20 according to one example of the present application in a harvesting position and in an implantation position, respectively. The harvesting procedure requires the patient to be face down, while the implantation procedure is a face-up procedure. One advantageous feature of the hair transplantation chair described herein is the ability to easily convert it between the harvesting and implantation configurations. To reduce the chair space required in the treatment office, a chair capable of supporting both harvesting and implantation positions is especially useful. However, the capability of converting the chair does not preclude the provision of two separate chairs for the different procedures. It should be understood, therefore, that unless excluded by the claim language that the hair transplantation chair in different embodiments can be just for harvesting, just for implantation, or convertible between the two configurations.

The hair transplantation chair 20 is shown to include a stable base platform 22 configured for positioning on the floor and having a pair of substantially curved rails 24 fixed vertically thereon. The rails 24 commence at a low point at a rearward end 26 of the base 22 and curve upward in a forward direction to a high point 28 (see FIG. 2). A base of the chair 20 may include the base platform 22 and any elements mounted on it in a fixed manner, such as the rails 24 and an arc-shaped support 25 (shown in FIG. 2) that projects upward from the base platform. The directions forward and rearward are arbitrarily assigned to the orientation of the patient in the implantation position shown in FIG. 2. A flat portion of the base 22 near the ground may be shaped and configured to allow a doctor come close to the sides of the patient, as seen in FIG. 1.

A cradle or carriage 30 includes a lower bracket 32 that travels on the curved rails 24. The carriage 30 thus moves in either direction along a generally arc-shaped path indicated by the double arrow 34 in FIG. 1. More particularly, the cradle 30 rotates or pivots along a generally arcuate surface defined by the rails 24 on the base 22. Rotational or pivoting movement of the cradle is substantially centered about a point mark with a letter C. A particular height or a range of desired heights of point C may be chosen depending on particular embodiment or implementation to accommodate sitting/standing position that is comfortable for a physician during procedure, adequate space available for the comfort of the patient, and/or to accommodate the clearance needed for the robot in order not to interfere with the head of the patient. In the embodiments directed to hair harvesting and/or implantation procedures, the point C is located in close proximity or substantially close to the center of the patient's head when it is positioned on a head support or a headrest of the chair. Therefore, the cradle 30 rotates substantially about the patient's head positioned on the head support with a minimum change in elevation or translation (forward and back movement within a horizontal line). It shall be understood that the pivoting point C may be located within a small distance of the center of the head, for example, within 0 to 3 inches radius, and in some embodiments preferably within 0 to 1 inches radius. Furthermore, as seen in FIG. 1, a number of adjustable supports (with optional cushions) may be attached to the cradle 30.

First of all, the patient P is shown with his head slightly elevated from a head support 40 that is attached at the top of a generally vertical or upright column 42. It should be noted that hair transplants are more often done on males, and therefore the patient P will be referred to in the masculine sense simply for convenience of the description. It should be understood that the same should apply to the female patients. The head support 40 may include a central opening that receives the patient's face and permits breathing and vision during the long procedure with a face down. Soft cushioning is typically provided on the head support 40, though it is not shown in this illustration. One of the goals of the chair is to maintain patient comfort and procedural efficiency, which at least in part is contributed by effective head and neck adjustments. These adjustments are important because they affect an ease of positioning a tool used for harvesting or implantation relative to the donor or recipient area on the head of a patient. The head support 40 may be adjustable relative to the column 42 to have the ability to translate forward or backward, or pivot in a vertical plane aligned with the forward backward directions. Such adjustment will provide for different head orientations and angling while seating in the chair, and accommodate patients with different head shapes and neck length. For example, in some non-limiting embodiments the head support is configured to pivot ±22.5 degrees, as well as translate forward or backward ±1.5 inches (a total of 3 inches). In other embodiments, these dimensions may vary. The translational motion of the head support may be achieved, for example, by using linear slides that are located within a frame of the head support, or, for example, a four bar linkage mechanism could achieve similar movement. Locking clamps (not shown) may secure the position and orientation of the head support 40 with respect to the column 42. Once the headrest pivoting and sliding in forward/backward direction is fixed and locked for a particular position of a patient during at least a portion of the procedure, it is desirable that such fixed headrest position remains substantially the same during that portion of the procedure. For example, once the head of the patient is positioned for harvesting all desired hair grafts from a certain region of a head, it is desirable that the head will remain in that position during the whole time that is needed for harvesting all selected hair grafts from that region. Therefore, harvesting or implantation from that selected region of the scalp will occur without further movements of the head support 40. However, to improve comfort of a person positioned in the chair without allowing movements of the head support (and ultimately, the head) for a prolonged time, the overall position of the body of the person and/or position of the other body supports may be adjusted to enable slight movements during that time and relieve muscle stress or discomfort, as will be described.

In the harvesting position of FIG. 1, the hair transplantation chair 20 may include a padded arm support 44 mounted on or attached to the column 42. A torso or chest support 46 (typically padded) may be also mounted on the column 42. In the embodiment of FIG. 1, the patient P sits on a seat 48 (that may be padded) and may rest his knees on padded leg rests 50 on either side of the cradle or carriage 30. As indicated, each of the described supports may be operatively attached with respect to the cradle/carriage 30, although their respective positions may be adjusted in various ways as needed. Any of the supports may be padded or non-padded in various embodiments and implementations.

More particularly, in some embodiments the arm support 44 may be adjusted vertically with respect to the column 42. Similarly, the torso support 46 can be pivotally adjusted to change the angle with respect to the column 42. The height and angle of the seat 48 also can be adjusted, as can the angle of the leg rests 50. However, because the carriage 30 rotates about position in close proximity or substantially near a center of the head positioned on the head support 40, any of these supports, that may be referred to as the body supports, can be adjusted during the procedure to change the posture or a weight allocation of the patient P without the patient's head substantially moving. In other words, the entire carriage 30 can be shifted along the rails 24 to reorient the angle of the patient (and to shift his/her weight allocation), while the head support 40 remains substantially stationary (although some, for example, pivoting adjustments to accommodate the angle of the neck are allowable) because it sits close to the center C of rotation of the carriage. If desired, the various supports may be also adjusted to make the patient more comfortable in the new position, however, once initially adjusted to accommodate for a particular patient, subsequently a slight pivoting or rotation of the cradle alone may provide all relief necessary to the patient to avoid discomfort and muscle strain.

FIG. 2 shows the hair transplantation chair 20 re-configured for an implantation procedure. The carriage 30 is shown rotated about the arc centered at point C to a rearward position relative to the base 22 and rails 24 such that the column 42 is at the far rear end of the system. The head support 40 mounts at the top of the column 42, and the torso support 46 is repositioned to support now the upper back of the patient P. The patient sits on the seat 48 and a supplemental lumbar support 52 may be attached, for example, to the underside of the seat 48 for additional support. The seat 48 further includes padded armrests 54. Either the arm support 44 or the leg/knee rest 50 shown in FIG. 1 may be decoupled from the system and reattached to provide an angled leg support 56 as seen in FIG. 2. Reattachment of various body supports can be achieved, for example, by quick release fasteners, they could be also adjusted by pivot angles and/or slots for linear positioning.

Figure 3:
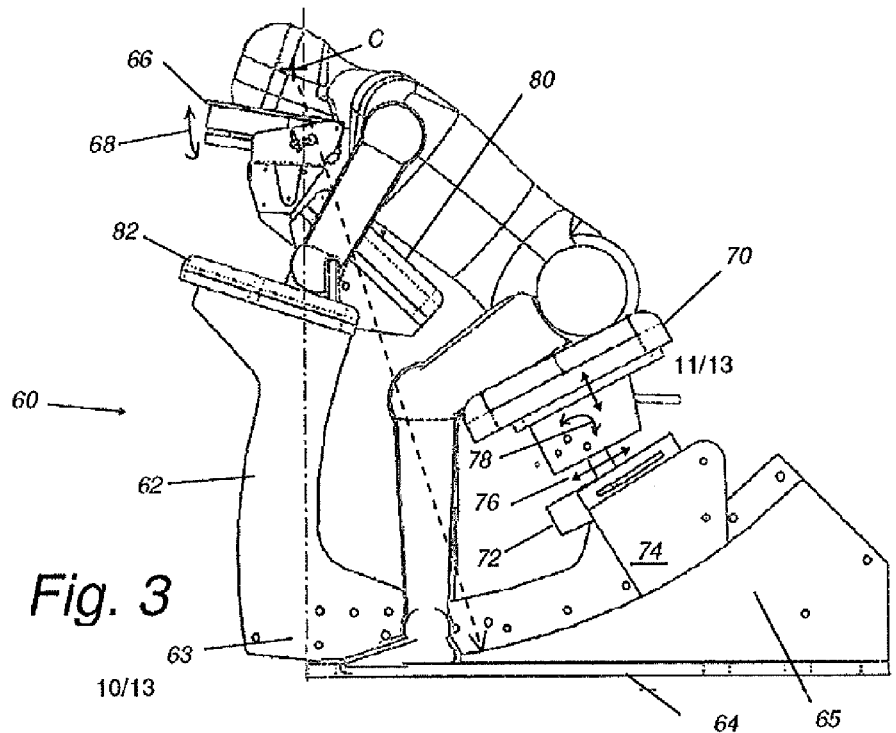
FIG. 3 is an elevational view of a patient positioned in an adjustable hair transplantation chair configured for harvesting according to another embodiment.
Figure 4:
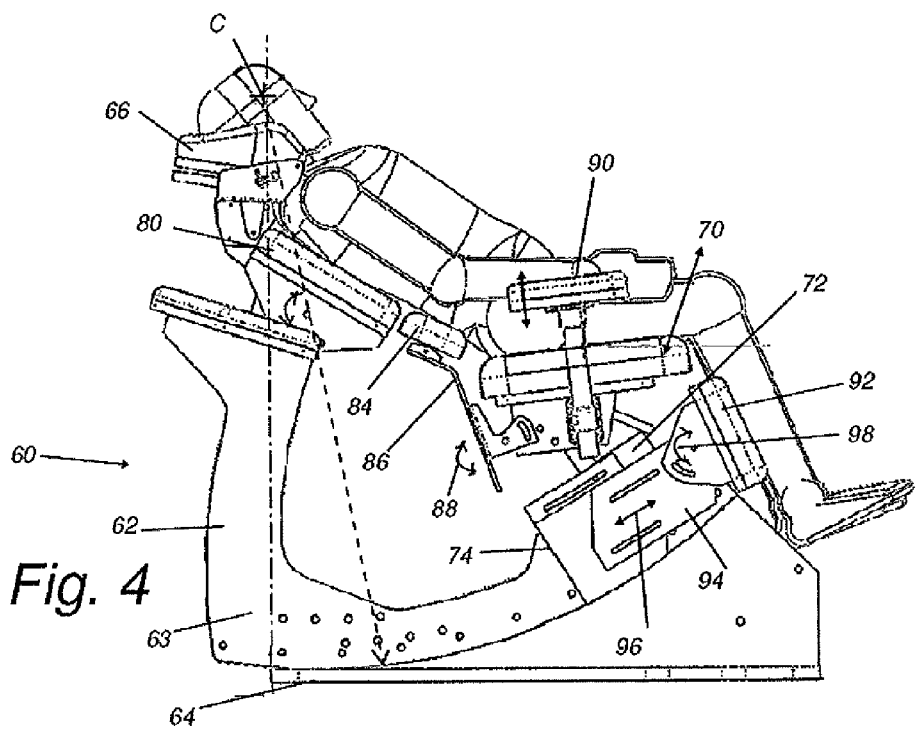
FIG. 4 is an elevational view of the patient in the hair transplantation chair re-configured for implantation.

FIG. 3 is an elevational view of a patient positioned in an example of an adjustable hair transplantation chair 60 configured for harvesting, and FIG. 4 is an elevational view of the patient in the hair transplantation chair 60 re-configured for implantation. Comparison of FIGS. 3 and 4 will indicate to the reader the conversion of various supports between the harvesting and implantation positions.

In the hair transplantation chair 60, a column 62 extends generally upward on a cradle 63 (and may form a part of a cradle). The cradle 63 is configured to move along a generally arc-shaped path on a base 64. As mentioned previously, the base 64 of the chair 60 includes any elements mounted thereto in a fixed manner, such as a support 65 that projects upward from a lower platform, and may include rails or a track (not shown) on which the cradle 63 rotates or moves. A head of the patient, if positioned on the head support 66 at the top of the column 62, will remain substantially at the same spatial location (from the elevation and/or translation point of view) with respect to the base 64 because the arc of rotation of the cradle 63 is centered adjacent thereto; however, the angle of the head support 66 may be adjusted as indicated by the double-headed arrow 68, as explained in more details earlier. In the harvesting position of FIG. 3, the patient P sits on a padded seat 70 with his feet on the floor. Also, the head support 66 features a padded rest having a central opening that receives the patient's face and permits breathing and vision thereby during the long procedure. The head support may use pads of various thickness, therefore, depending on the size/thickness of the pad, in some embodiments the height of the head support may be adjustable so that the elevation/height of the position of the head of the patient P on the padded head support remains substantially the same.

The padded seat 70 may be pivotally mounted on a seat carriage 72 that in turn mounts to translate linearly or along a slight arc with respect to a bracket 74 as indicated by double-headed arrow 76, the bracket 74 could be mounted to the cradle 63. Indeed, the seat carriage 72 may also rotate along the same arc as the cradle 63, with a center at point C. The padded seat 70 may, for example, tilt or pivot ±20° with respect to the seat carriage 72, as indicated by the double-headed arrow 78. The seat 70 may also be adjusted in height, for example, up to 5 inches both up and down, and it could be translated forward/backward a total distance of 3 inches. The patient's chest rests on a torso support 80 that may pivot ±45° with respect to the column 62. A padded armrest 82 may be attached in a fixed position to the column 62, however, it also may be adjustably positioned.

With reference now to FIG. 4, the hair transplantation chair 60 has been converted to the implantation position with the patient in a face-up orientation. The seat carriage 72 has been moved to the right, or in a counterclockwise direction. The angle of the padded seat 70 has been re-oriented and a supplemental lumbar support 84 attached to a bracket 86 may be mounted to an underside thereof. Further, the pad for the head support 66 has been switched from the open-faced version for harvesting to a bowl-shaped pad to support the back of the patient's head during implantation. The bracket 86 may be attached to pivot about an axis as indicated by the double-headed arrow 88. The torso support 80 is now an upper back support that has been re-oriented to align with the lumbar support 84. Finally, a pair of armrests 90 and a single or bifurcated leg rests 92 are added for patient comfort. The armrests 90 may be vertically adjustable, for example, ±6 inches, while the leg rest 92 may be mounted to a bracket 94 that slides on and may be locked with respect to the larger bracket 74, as indicated by the double-headed arrow 96. Further, the leg rest 92 may pivot about the bracket 94 as indicated by the double-headed arrow 98.

In both the harvesting position of FIG. 3, and implantation position of FIG. 4, the hair transplantation chair 60 provides a plurality of movable body supports. It is desirable that the head support 66 generally retains its position with respect to the floor or the bottom portion of the base 64, while the seat 70 rotates around it. In each position, the various padded body supports and rests are also adjusted to maximize patient comfort. In this manner, a long procedure of perhaps several hours may be performed without unduly causing discomfort to the patient. For example, during the harvesting or implantation procedure, the cradle 63 and/or seat 70 may be moved along their respective arcs, while any of the supports (e.g., 80, 84, 90, and 92) may be translated, pivoted, or adjusted in height and orientation as appropriate. The patient's posture can therefore be adjusted during the procedure without changing the spatial position of the head on the head support 66.

FIGS. 5A and 5B are perspective views from opposite sides of another example of an adjustable hair transplantation chair 100 of the present application in a harvesting position, while FIGS. 8A and 8B show the chair 100 re-configured into an implantation position. These two positions are also shown in the various orthogonal views of FIGS. 10A-10D at 11A-11D.

The hair transplantation chair 100 includes a base 102 adjustably mounted on wheels 104 as described in more detail in reference to FIGS. 9A-9C. Although the base 102 can be stationary, in some embodiments it may have wheels. The wheels 104 permit the chair 100 to be easily transported and also to be moved from one procedure room to another, as needed. As will be described, the wheels 104 are desirably convertible so that the chair 100 can rest on the underside of the base 102 or on the leveling feet during any one procedure for stability.

As seen in FIG. 5A, the base 102 includes a frame 106 that projects upward on one side and defines a generally arc-shaped path for sliding/rotational/pivoting movement of a cradle or carriage 108. At least a portion of the cradle 108 has a generally arcuate shape generally conforming to the arc of the frame 106. The cradle may be moved along an arc having a length, for example, of 15 to 20 inches and subtending an angle in the region of, for example, 24 to 30 degrees with respect to the center of rotation C. The cradle 108 also includes a column 110 projecting upward at one end thereof.

Figure 10D:
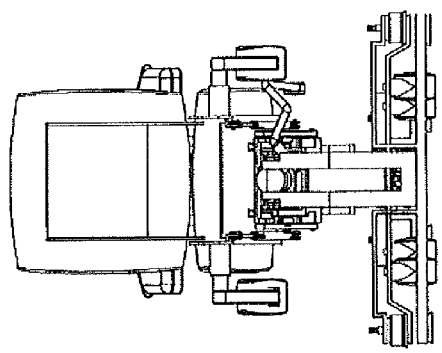
FIGS. 10A-10D are various orthogonal views of an alternative embodiment of a hair transplantation chair in a harvesting position.
Figure 10B:
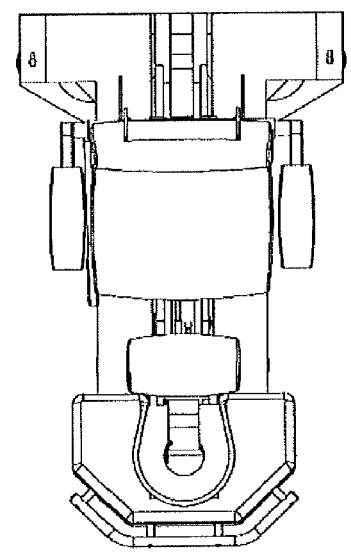
Figure 10C:
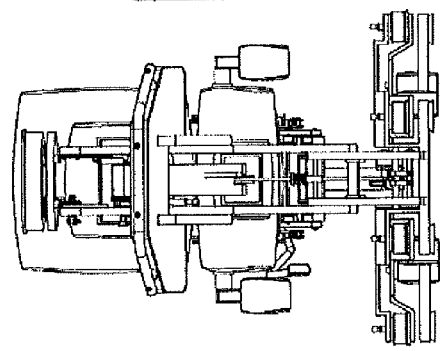
Figure 10A:
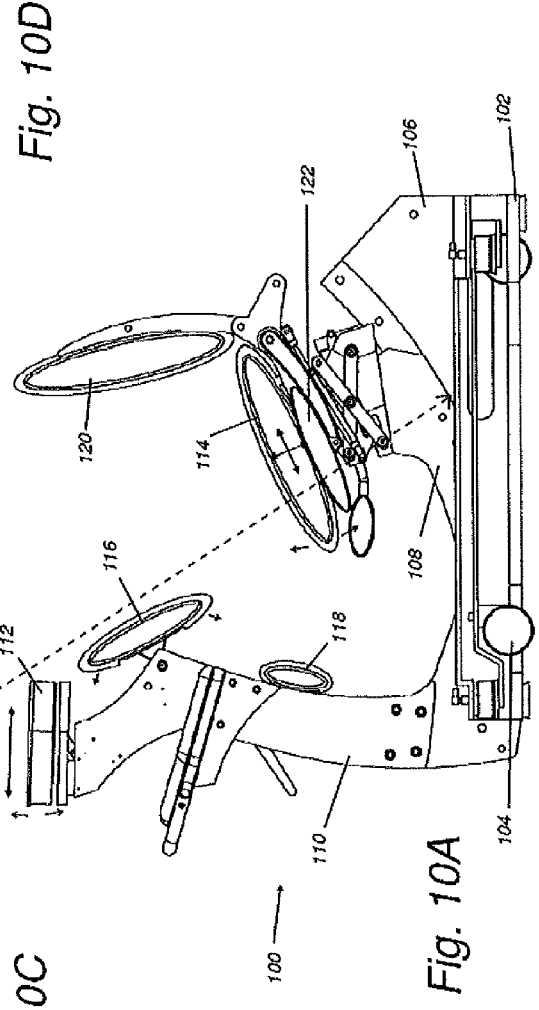
Figure 11D:
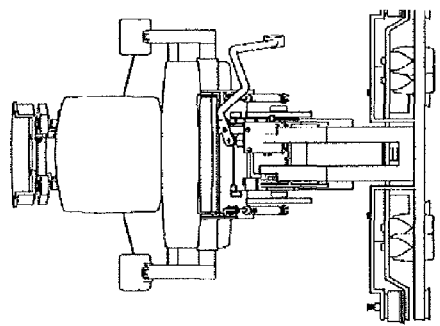
FIGS. 11A-11D are various orthogonal views of an alternative embodiment of the hair transplantation chair in an implantation position.
Figure 11B:
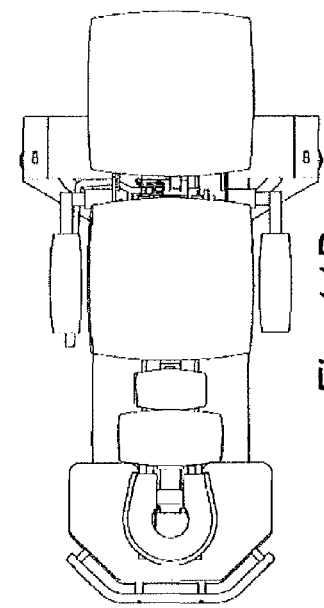
Figure 11C:
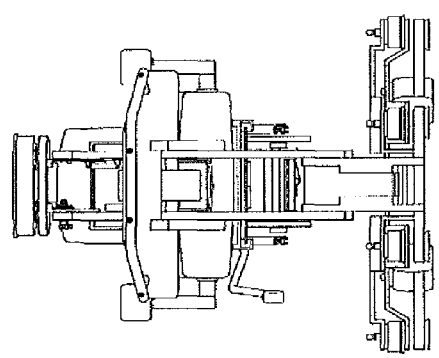
Figure 11A:
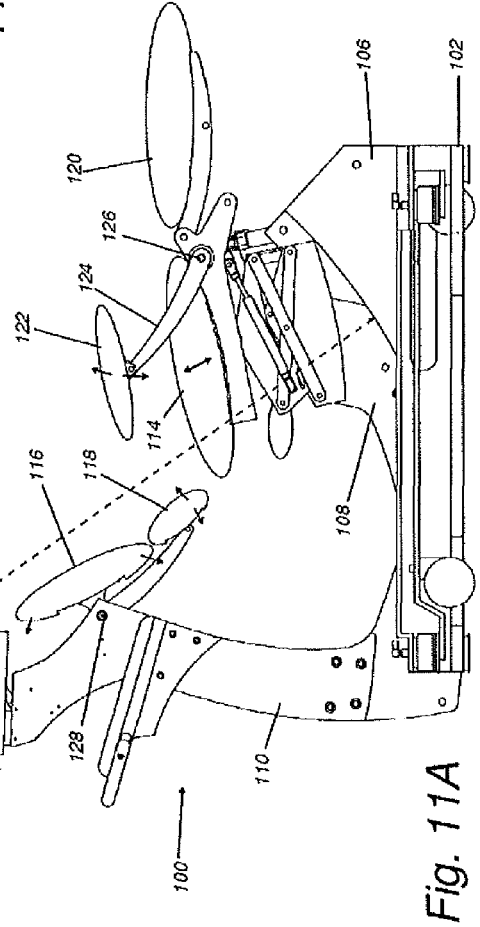

As could be also seen in FIGS. 10A and 11A, a head support 112 mounts at the top of the column 110. As seen in FIGS. 10A and 11A, various other body supports are provided on the chair 100, including a seat 114, a chest or back support 116, and lumbar support 118, a leg rest 120 (see FIG. 11A), and a pair of armrests 122. In the harvesting position shown in FIG. 10A, the patient lies face down with his posterior resting on the seat 114, his chest on the chest support 116, and his head on the head support 112. In implantation position of FIG. 11A, the patient lies face up with his posterior resting on the seat 114, is back on the back support 116 and additional lumbar support 118, and his legs on the leg rest 120. In some embodiments (as seen in FIGS. 5B and 8B), an additional leg (e.g. calf) support portion 123 may be provided for supporting ankles. The armrests 122 are typically raised in the implantation position, as seen in FIG. 11A, but lowered in the harvesting position.

Each of these supports and rests are independently movable in at least one direction. For example, as seen in FIG. 11A, the armrests 122 pivot on an arm 124 about a point 126 fixed with respect to the seat 114. The chest or back support 116 pivots about a point 128 fixed with respect to the column 110. Likewise, the head support 112 may be translated left or right (forward/backward) relative to FIGS. 10A and 11A, and tilted up and down as indicated by the arrows.

Each of the supports/rests may be connected or mounted for movement relative to the cradle or carriage 108. The carriage 108 in turn rotates about the arc defined by the base frame 106. That arc is centered about a point C that may be positioned in close proximity, for example, slightly above the head support 112. In other words, the collection of the supports/rests defines a frame of reference that rotates substantially about the head of a patient when positioned on the head support 112. As seen in this embodiment, although the individual support/rests may be adjusted within a certain range, they ultimately rotate or are mounted to a point that is fixed on the carriage 108. Because the carriage 108 rotates about the head support 112 as previously explained, anything mounted thereon also rotates about the head support. One of the additional advantageous of this configuration is that the chair 100 may be converted from the harvesting configuration to the implantation configuration and back by moving the carriage 108 and adjusting the various supports, while the head support 112 may remains substantially in the same position. Likewise, during either the harvesting procedure or implantation procedure, the patient's body positions can be adjusted by moving one or more of the supports/rests, with the head of the patient remaining relatively stationary on the head support 112.

FIGS. 6A and 6B illustrate just the seat 114 of the hair transplantation chair that may be implemented in various embodiments of the present application, and an example of a mechanism 130 for elevating the seat. The mechanism 130 changes the elevation of the seat 114 relative to the cradle and/or the base of the chair. For instance, a locking knob 132 accessible on the end of an arm permits the user to loosen a clamp that fixes the chair elevation. In some embodiments, springs (not shown) within the support mechanism 130 may bias the seat 114 upward, so that the user need only reduce the weight on the seat and loosen the knob 132. The springs have a force less than the expected patient weight, so that the seat 114 can easily be lowered by loosening the knob 132 and sitting on the seat. This adjustment provides flexibility to the hair transplantation chair to accommodate both small and large patients. In some embodiments a hydraulic cylinder may be used to adjust the height of the chair. To raise the height of the chair the user may pump a handle, for example, the handle of the knob 132, up and down to the desired height. To lower the chair the user may rotate the knob 132 at the end of the handle to release the pressure in the system, then may tighten the knob at the desired height. Of course, various other mechanisms 130 are contemplated, such as a pneumatic or hydraulic system, a crank lift, a lever such as with a car jack, foot pump, etc.

According to another aspect, FIG. 7A shows an embodiment of a cradle movement mechanism, for example a crank adjustment mechanism, that may be implemented with various embodiments of the chair of the present application for rotating a cradle, for example, the cradle 108 of the hair transplantation chair 100. The mechanism features a handle or crank 142 that may be mounted or attached to or within the frame 106 (fixed to the base 102) and connected to a shaft 144 that either turns a gear within a gearbox or acts on a pneumatic or hydraulic driver 143. Alternatively, as will be understood by those of skill in the art, the 142 crank may be mounted to the cradle 108. Turning the crank 142 displaces the cradle 108 with respect to the frame 106. Prior to displacing the cradle 108, its position must be unlocked with respect to the frame 106. In particular, FIG. 7B shows a lever 146 (also seen in FIG. 5A) that may be mounted to the column 110 and connects through a series of linkages 148 to a brake (not shown) for the cradle 108. When the technician or surgeon desires to reposition the patient, he/she manipulates the lever 146 to permit unlocking of a locked position, and then displaces the cradle 108 by turning the crank 142. Rotation of the cradle is accomplished by turning the handle 142 to desired angular position. The cradle is held in that position via a worm gear. The worm gear prevents the cradle from moving unless purposefully moved with the crank 142. The function of the brake mechanism shown in FIG. 7B is to eliminate any undesirable play in the cradle mechanism and to provide a solid and rigid connection such that there is no significant movement in the structure that could be translated into the head support. It is desired to have a substantially stable head support. For example, in some embodiments the head support can deflect no more than 0.10 inch at 10 lbs of perpendicular force. This will provide stability of the head positioned on the head support in the acceptable range, especially when implemented with the use of robotic systems for hair transplantation or other robotic systems. The cradle 108 can be moved in any desired infinite increment per turn of the crank 142, for example, in some embodiments in the range of up to 36 degrees of movement. In other implementations, the range of the degrees of movement may be adjusted up or down as applicable in that particular implementation. If desired, in certain embodiments the adjustment increments may be set at a certain resolution, for example, at a resolution of 1°. In some embodiments it may be desirable to use a marking or indexing system, for example, for the adjustment increments so that a doctor or technician may pre-set the cradle position based on previous experience with various patients, for example, historic data of positions preferred by previous patients. Such markings may be visible marks. Alternatively, an indexing may be implemented by entering a desired increment electronically, for example, using a processor associated with the chair. Using such pre-set positions will save procedure time during cradle adjustment. Similar marking or indexing system could be applied, as appropriate, to any other adjustments of the body supports of the adjustable chair of the present application. Of course, the above-described operations can be automated with electric motors, pneumatics, hydraulics, foot pumps and such, and the particular mechanism for locking and displacing the cradle 108 is exemplary only.

In various embodiments of the chair, instead of being stationary positioned on the ground, the chair may be provided with a plurality of wheels to allow the chair to be moved to a different room or a floor of the medical facility. While it may be desirable to easily move the chair when needed, it is also desirable to provide stability to the chair during procedure on a patient. Therefore, according to another aspect of the present application, in some embodiments the chair may be provided with the adjustment mechanism to position the chair, for example, either on leveling feet when stability is desired, or on the moving wheels when it is desirable to move the chair. Now with reference to FIGS. 9A-9C, an example of an adjustment structure for the wheels (casters) 104 is shown. The wheels 104 each may bolt to a member 150 that moves up and down within a housing 152 which may be fixed to the base or frame. In particular, each member 150 includes a pair of vertically-oriented pins 154 on opposite sides thereof that slide within a vertical slot 156 and housing 152. A variety of devices can be used to displace the members 150 up and down within the housing 152; one particularly useful version is a foot pump 158 seen in FIG. 8B that inflates an air bladder (not shown) to simultaneously move all members 150 (for example, four members) down within the respective housings 152 and lift the whole chair. Conversely, when all four members 150 are raised up to elevate the wheels 104, the chair 100 may rests on the base 102, or more preferably, on leveling feet 159 depending below the base 102. At least one of the leveling feet 159 may be threaded into a socket under the base 102 so that it may be independently adjusted to stabilize the chair 100 on variously contoured floors. The lift mechanism 153 will raise and lower the entire chair off its leveling feet so that it can be moved into a new position, including transporting to another room. The feature of lowering or raising movable casters (wheels) allows the chair to obtain repeated stability. Also, the use of an air bladder lift mechanism improves the ability of the wheels to roll over small objects while moving the entire chair by virtue of the shock absorption properties of air.

Figure 12B:
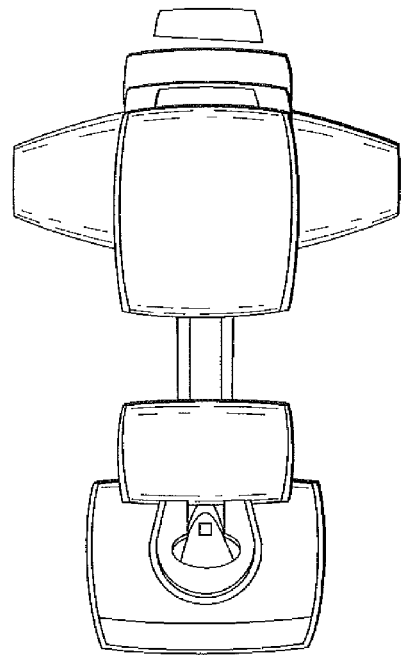
FIGS. 12A-12C are perspective and orthogonal views of yet another alternative adjustable hair transplantation chair of the present application in a harvesting position, also illustrating a robotic system used for automated hair transplantation.
Figure 12C:
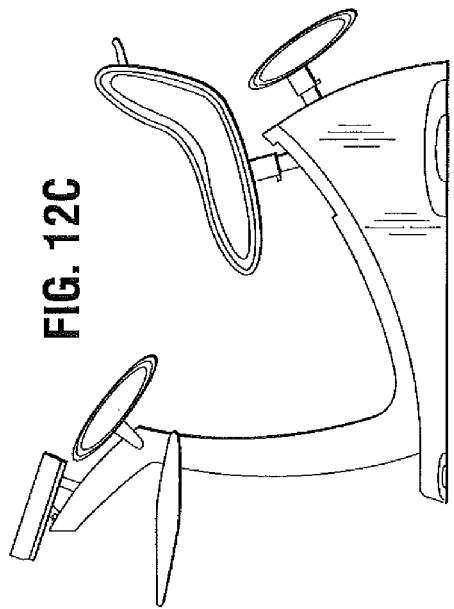
Figure 12A:
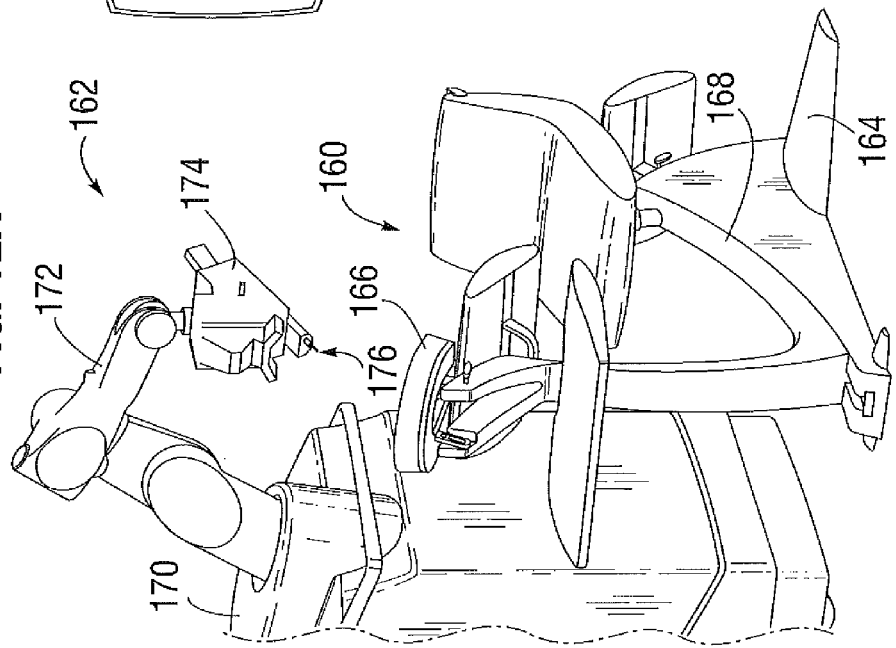

FIGS. 12A-12C illustrate an alternative adjustable hair transplantation chair 160 of the present application in a harvesting position, while also illustrating a robotic system 162 used for automated harvesting. The chair 160 and robotic system 162 are also shown in FIGS. 13A-13C in an implantation position. The hair transplantation chair 160 is similar to those described above, and includes a base 164. As before, a cradle or carriage 168 may rotate/pivot along a portion of an arc with a center of such rotation/pivoting at a point adjacent or substantially near the head support 166 as previously explained in reference to other embodiments. In this manner, the overall position of the patient can be adjusted during each procedure without a need to substantially moving the head support 166, and also the chair can be converted between the harvest and implant positions.

The robotic system 162 illustrated by example in FIGS. 12A-12C has a cart 170 on which a robotic arm 172 is mounted. A tool assembly 174 may be coupled, for example, to the distal end of the robotic arm 172. The tool assembly 174 comprises a tool, such as a harvesting tool or implantation tool, with an operating tip 176. Various motors and other movement devices may be incorporated to enable fine movements of an operating tip 176 of the tool in multiple directions. The robotic system 200 may further include at least one image acquisition device (not shown). A computer (not shown) may instruct the movement of the robotic arm 172 and also various movements of the tool assembly 174. The computer may comprise a processor which may act, for example, through a controller that may be operatively coupled to the robotic arm 172 and configured to control the motion of the robotic arm, including the motion based on the images or data acquired by the image acquisition device. The system 162 may further comprise a monitor, keyboard, mouse, and other tools, devices and components useful in harvesting, and/or implantation of the hair follicles, or in hair treatment planning (also not shown). Various robotic hair transplantation systems, described for example, in the commonly-assigned patent publications of the assignee of the present application, such as U.S. Patent Publication No. 2007/0106306 to Bodduluri et al., may be implemented with various embodiments of the present application.

Figure 14C:
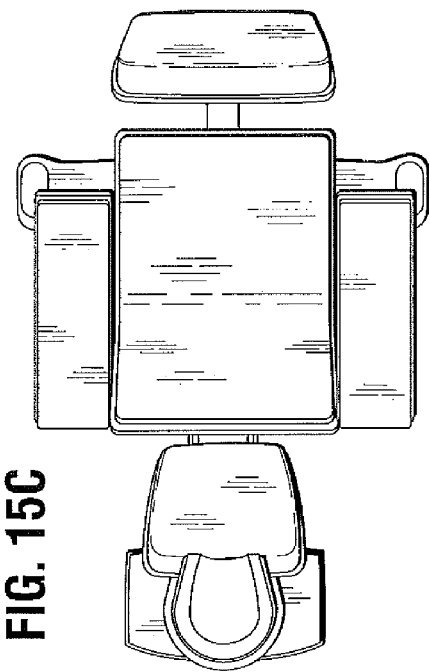
Figure 14B:
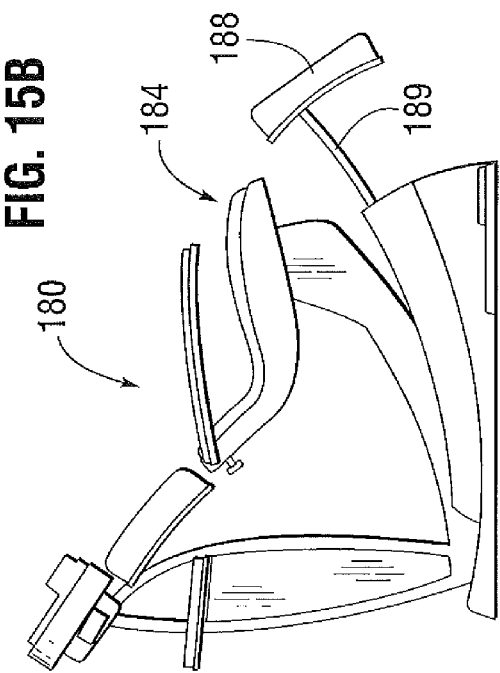
Figure 15C:
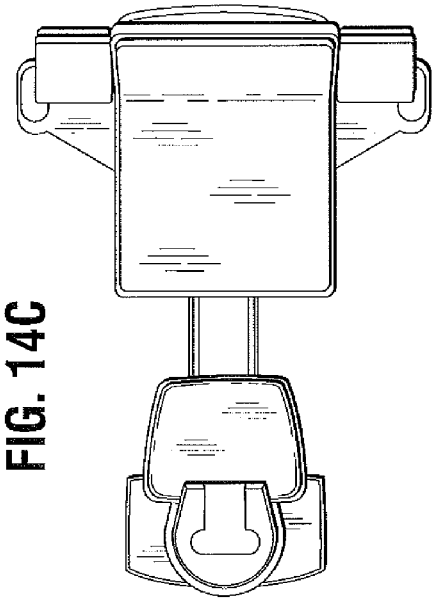
Figure 15B:
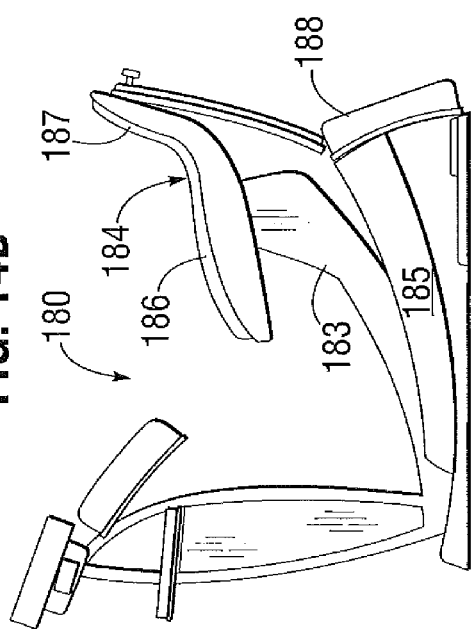

FIGS. 14A-14C show an alternative adjustable hair transplantation chair 180 of the present application in a harvesting position, while also illustrating a robotic system 182 used for automated harvesting. The chair 180 and the robotic system 182 are also shown in FIGS. 15A-15C in an implantation position. The chair 180 includes several features previously not shown. For example, a cradle 183 on which a seat 184 mounts elevates somewhat above a base 185. This emphasizes that the "cradle" may be a relatively bulky arc-shaped member as previously shown, or it may comprise a more elegant support such as the cradle 183. Furthermore, the seat 184 includes a seat portion 186 and a backrest 187, thus combining two of the supports that were previously described as being separate. An additional feature is a leg rest 188 that may be used in the implantation configuration of the chair 180 such as shown in FIG. 15B. The leg rest 188 may be attached to a sliding arm 189 that is collapsible relative to the base 185 when the leg rest 188 is not in use, such as shown in the harvesting configuration of FIG. 14B. Moreover, the ergonomics of the chair 180 represent an alternative aesthetic appearance of the chair.

Figure 17A:
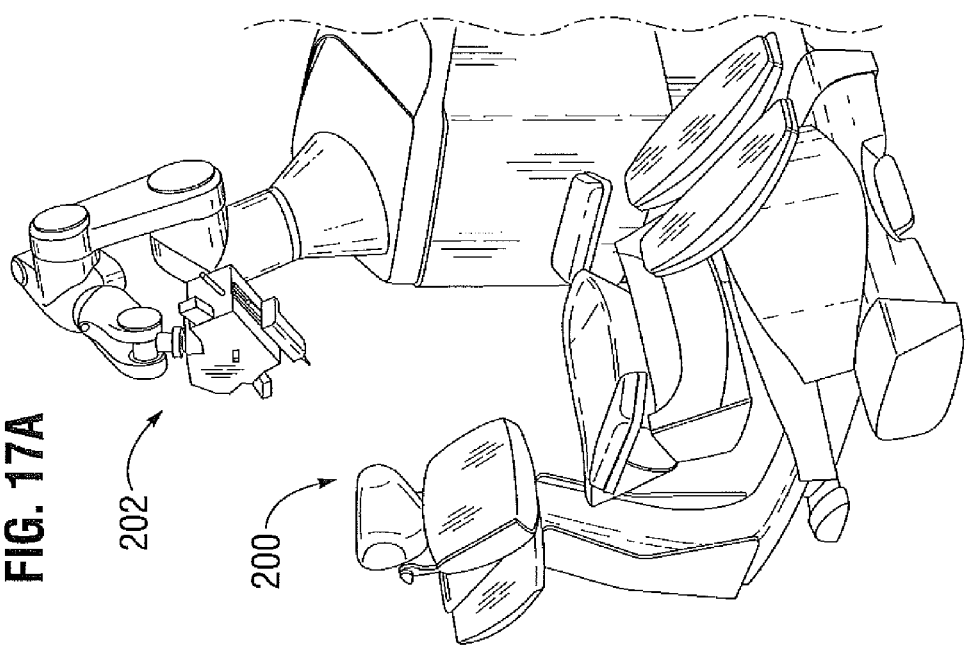
Figure 16A:
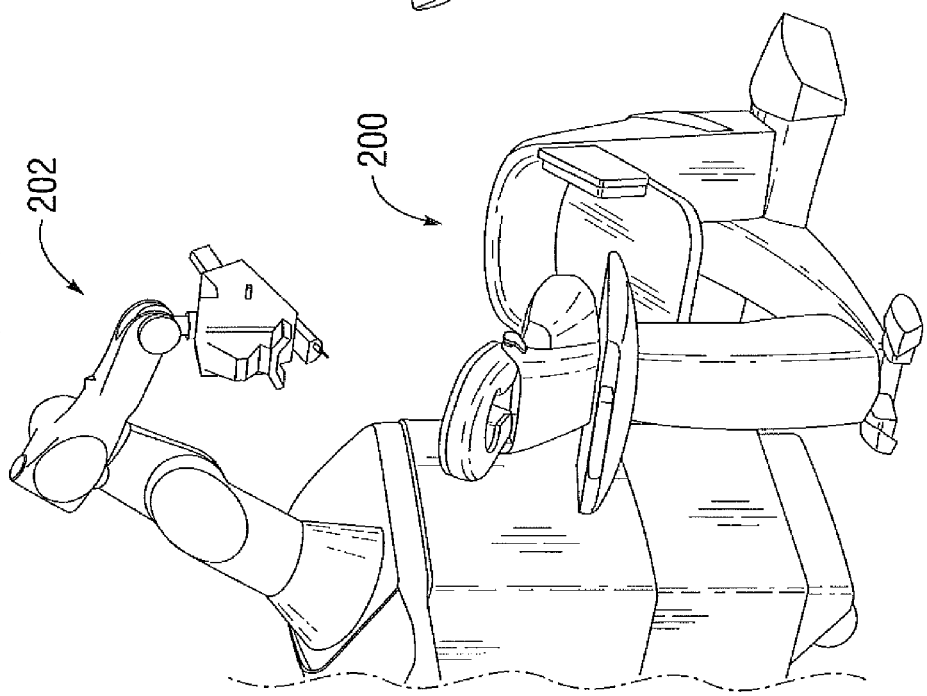

A further alternative adjustable hair transplantation chair 200 of the present application is seen in FIGS. 16A-16C in a harvesting position, and in FIGS. 17A-17C in an implant position. An example of the robotic system 202 used for automated harvesting and implantation is also shown. The hair transplantation chair 200 includes a bifurcated leg support 204 that permits individual adjustment as desired. Also, a seat support 206 may convert between the harvesting configuration of FIG. 16B and the implantation configuration of FIG. 17B by swiveling. The reader will notice that the arc of travel of a cradle 208 has a center of rotation or pivoting C located above the cradle, substantially fixed relative to the ground and located in close proximity to a head support 210. As explained previously, this permits a person located in the chair to adjust his/her overall position and/or adjust various supports in both the harvesting and implantation configuration to be moved around for patient comfort during the long procedure without substantially changing the absolute position of the person's head while resting on the head support 210.

Figure 18A:
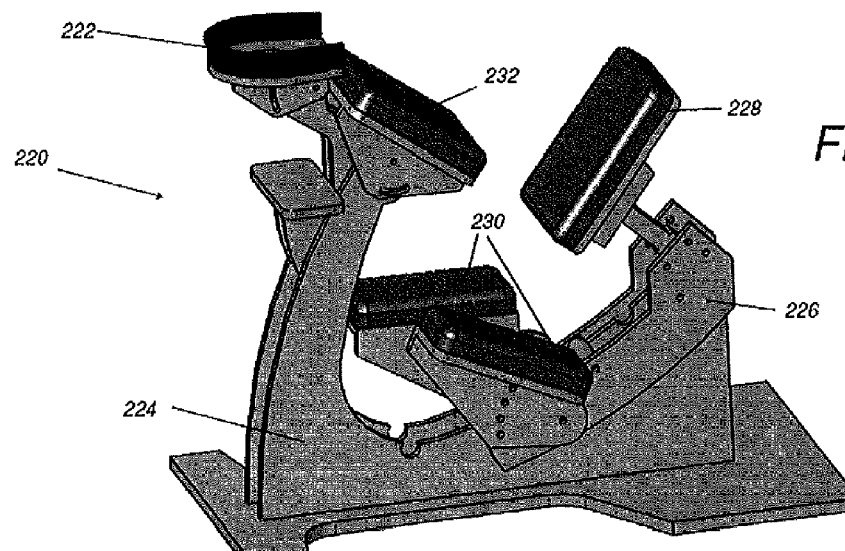
FIG. 18A is a perspective view of a further alternative embodiment of an adjustable hair transplantation chair in a harvesting position.
Figure 18B:
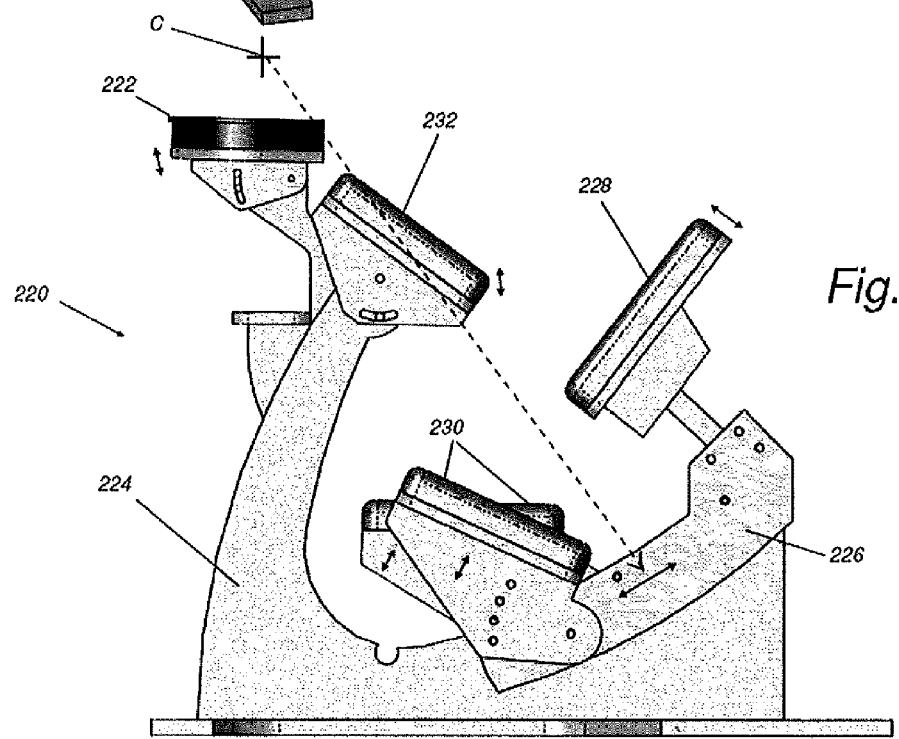
FIG. 18B is an elevational view of the same chair.

FIGS. 18A and 18B illustrate yet another alternative adjustable hair transplantation chair 220 in harvesting configuration. The chair 220 differs in that a head support 222 is shown to be mounted on a column which forms a part of the base 224, rather than on a cradle 226 that moves on the base. The column may be located near one end of the base 224 while the cradle 226 may be positioned away from that end of the base. Because the cradle 226 (and the seat 228 attached to the cradle) moves along a generally arcuate path that has a center of rotation C in a proximity to the head support 222 (e.g., slightly above the head support 222 in FIG. 18B), movement of the cradle and readjustment of various other patient supports generally will not involve movement of the person's head when positioned on the head support 222. As before, however, the head support 222 may be mounted for various relatively small movements, for example, an elevational, translational and/or tilting movement, and thus may be adjusted during the procedure, as long as the position of the head when placed on the head support remains substantially close to the center of rotation of the cradle.

In the illustrated embodiment, the hair transplantation chair 220 includes a seat 228 mounted on the cradle 226. In some embodiments, if desired, a pair of optional separate knee supports 230 may be also mounted on the cradle 226. A chest or back support 232, depending on whether the chair is configured to harvesting or transplantation, may be mounted on the base 224, for example, on a column which is fixed or forms a portion of the base 224. In this manner, the various supports can be adjusted to relieve patient discomfort during long procedures without substantially changing the absolute position of the person's head on the head support 222. Although not shown, the hair transplant chair 220 can be converted as with the other embodiments into the site making or implantation position.

The present application also provides various methods for adjusting a chair of the present application, and for performing a hair transplantation procedure. One such method comprises performing a hair transplantation procedure using a convertible hair transplantation chair. The method comprises positioning a patient in a convertible hair transplantation chair in a harvesting configuration of the chair wherein a patient's posterior rests on a seat leaning forward with a head of the patient positioned face-down on a head support; harvesting follicular units from the patient positioned in the harvesting configuration of the convertible chair; converting the hair transplantation chair to an implantation configuration where the patient's posterior rests on the seat leaning backward with his head positioned face-up on the head support; and implanting hair grafts into a recipient area of the patient in the implantation configuration of the convertible chair. In some embodiments the convertible chair comprises a cradle mounted on the base and configured for rotation along an arcuate path having a center located above the cradle and in close proximity to a center of the head of the patient positioned on the head support, and converting the chair to the implantation configuration comprises adjusting position of the cradle along the arcuate path such that the center of the head of the patient on the head support remains approximately at the center of the cradle rotation. In some embodiments of the method converting comprises turning a portion of the seat in the harvesting configuration of the chair into a leg support in the implantation configuration of the chair. The above-mentioned method of performing hair transplantation procedure may be adjusted as needed for other procedures that could benefit from the same principles disclosed herein, and these alternative methods are contemplated within the scope of the inventions disclosed herein.

Another example of the method of performing a procedure (e.g. hair transplantation procedure) is a method comprising positioning a patient in a chair, the chair having a head support for receiving the patient's head in either a face-down orientation or a face-up orientation, the chair further including a cradle mounted on a base and configured for rotation along a substantially arc-shaped path having a center located above the cradle, wherein the head support is mounted such that when the patient's head is positioned on the head support, it is approximately at the center of cradle rotation, and wherein a seat is mounted on the cradle such that the patient may be seated thereon with his or her head on the head support, the position of the cradle on the base being adjustable along the arc such that the center of the patient's head positioned on the head support remains approximately at the center of cradle rotation. The method further comprises adjusting position of the cradle along the substantially arc-shaped path relative to the base. In some embodiments, the chair may be a hair transplantation chair, and the method may further comprise in some embodiments harvesting follicular units from the patient and in other embodiments implanting follicular units while the patient is positioned in the hair transplantation chair. The steps of adjusting position of the cradle along the path may be repeated as needed to reposition the patient in the chair, and then the steps of hair harvesting or hair implantation may be repeated while the patient is in the adjusted position.

With reference to various methods described herein, it will be apparent that the number of steps that are utilized for such methods are not limited to those described. Also, the methods do not require that all the described steps are present. Although the methodology described above as discrete steps, one or more steps may be added, combined or even deleted, without departing from the intended functionality of the embodiments of the invention. The steps can be performed in a different order or have the steps shared between more than one processor, for example. It will also be apparent that the method described above may be implemented using manual, partially or substantially automated systems, including using robotic systems.

While the invention has been described in its preferred embodiments, the words which have been used are words of description and not of limitation. These embodiments are susceptible to various modifications and alternative forms, and it should be understood that the invention generally, as well as the specific embodiments described herein, cover all modifications, equivalents and alternatives falling within the scope of the appended claims. By way of non-limiting example, it will be appreciated by those skilled in the art that particular features or characteristics described in reference to one figure or embodiment may be combined as suitable with features or characteristics described in another figure or embodiment. Further, those skilled in the art will recognize that the devices, systems, and methods disclosed herein are not limited to one field, such as hair restoration, but may be applied to any number of fields. Therefore, changes may be made within the appended claims without departing from the true scope of the invention. Applicant regards the subject matter of the invention to include all novel and nonobvious combinations and subcombinations of the various elements, features, functions, and/or properties disclosed herein.

What is claimed is:

1. An adjustable chair, comprising:
    a base;
    a cradle mounted on the base and configured for rotation along an arcuate path having a center of cradle rotation located above the cradle;
    a seat mounted on the cradle for supporting a person to be seated thereon; and
    the adjustable chair having a face down configuration in which the adjustable chair comprises a head support and a torso support, the head support
        1) configured to accommodate a head of the person face down while a torso of the person rests on the torso support and
        2) positionable on the adjustable chair such that a center of the head of the person, when positioned on the head support while the person is seated on the seat, is within 0-3 inches radius from the center of cradle rotation;
    wherein a position of the cradle on the base is adjustable along the arcuate path such that the head support remains substantially at the same spatial location as it was before the cradle adjustment along the arcuate path.

2. The adjustable chair of claim 1, wherein the head support is mounted to the cradle.

3. The adjustable chair of claim 1, wherein the head support is mounted to the base.

4. The adjustable chair of claim 3, wherein the base comprises a column near one end of the base and the head support is mounted on the column, and wherein the cradle is mounted away from the one end of the base.

5. The adjustable chair of claim 1, wherein the center of cradle rotation is positioned at an elevation of approximately 44 to 48 inches.

6. The adjustable chair of claim 1, further including a lock mechanism for locking the cradle relative to the base.

7. The adjustable chair of claim 1, further comprising one or more adjustable body supports mounted on the cradle such that when the cradle rotates along the arcuate path about the center of cradle rotation, the one or more body supports rotate with the cradle.

8. The adjustable chair of claim 1, further including a movement mechanism for displacing the cradle relative to the base.

9. The adjustable chair of claim 8, wherein the movement mechanism includes a crank.

10. The adjustable chair of claim 8, wherein the movement mechanism comprises an indexing system configured to allow adjustment of the cradle position based on previous experience.

11. The adjustable chair of claim 8, wherein the movement mechanism comprises a hydraulic system.

12. The adjustable chair of claim 1, wherein the head support is configured to translate forward and backwards.

13. The adjustable chair of claim 1, further including one or more body supports mounted on the cradle whose positions are adjustable relative thereto, and wherein at least one of the body supports comprise an adjustment mechanism with an indexing system that allows for pre-set adjustments.

14. The adjustable chair of claim 1, wherein the adjustable chair is configured to be convertible between the face down configuration and a face up configuration.

15. The adjustable chair of claim 1, wherein the adjustable chair has a face up configuration and the torso support is configured to convert to a back support in the face up configuration.

16. The adjustable chair of claim 15, wherein one or both of the back support and the torso support are movable relative to the head support.

17. The adjustable chair of claim 1, further including a plurality of wheels on which the adjustable chair is moveable, the wheels being retractable so that they may be elevated and the adjustable chair stabilized on the base.

18. The adjustable chair of claim 17, further comprising a lift mechanism.

19. The adjustable chair of claim 1, wherein the head support is adjustable to accommodate an angle of the person's neck.

20. An adjustable chair, comprising:
a base;
a cradle mounted on the base and configured for rotation along an arcuate path having a center of cradle rotation located above the cradle;
a seat mounted on the cradle for supporting a person to be seated thereon;
the adjustable chair having
1) a face down configuration in which the adjustable chair comprises a head support and a torso support and
2) a face up configuration in which the adjustable chair comprises the head support and a back support,
wherein in the face down configuration of the adjustable chair the head support is configured to accommodate a head of the person face down while a torso of the person rests on the torso support and wherein in the face up configuration of the adjustable chair the head support is configured to accommodate the head of the person face up while a back of the person rests on the back support, and
the head support is positionable on the adjustable chair such that a center of the head of the person, when positioned on the head support in either the face up or the face down configuration while the person is seated on the seat, is within 0-3 inches radius from the center of cradle rotation,
wherein a position of the cradle on the base is adjustable along the arcuate path such that the head support remains substantially at the same spatial location as it was before the cradle adjustment along the arcuate path and wherein the adjustable chair is configured to be convertible between the face down configuration and the face up configuration.

21. The adjustable chair of claim 20, wherein the adjustable chair is a hair transplantation chair and the hair transplantation chair is convertible between a harvesting configuration and an implantation configuration.

22. The adjustable chair of claim 20, wherein the torso support converts to the back support when the adjustable chair is converted from the face down configuration to the face up configuration.

23. The adjustable chair of claim 20, further comprising a lift mechanism configured to lift the adjustable chair onto a plurality of wheels.

24. The adjustable chair of claim 20, wherein in the face down configuration the head support further comprises a central opening that receives the person's face.

25. The adjustable chair of claim 20, wherein the head support is slidable and pivotable.

* * * * *